United States Patent
Baum et al.

(10) Patent No.: US 10,070,652 B2
(45) Date of Patent: *Sep. 11, 2018

(54) COMPOSITIONS AND METHODS FOR THE PRODUCTION AND DELIVERY OF DOUBLE STRANDED RNA

(71) Applicant: Monsanto Technology LLC, St. Louis, MO (US)

(72) Inventors: James A. Baum, Webster Groves, MO (US); Allen T. Christian, Wildwood, MO (US); Artem Evdokimov, Foristell, MO (US); Farhad Moshiri, Chesterfield, MO (US); Lisa Marie Weaver, O'Fallon, MO (US); Haitao Zhang, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,214

(22) Filed: Aug. 15, 2016

(65) Prior Publication Data

US 2017/0035056 A1    Feb. 9, 2017

Related U.S. Application Data

(63) Continuation of application No. 14/208,788, filed on Mar. 13, 2014, now Pat. No. 9,445,603.

(60) Provisional application No. 61/793,506, filed on Mar. 15, 2013.

(51) Int. Cl.

| | |
|---|---|
| *A01N 63/00* | (2006.01) |
| *A01N 65/00* | (2009.01) |
| *C12N 1/20* | (2006.01) |
| *C12N 15/00* | (2006.01) |
| *C07H 21/02* | (2006.01) |
| *A01N 63/02* | (2006.01) |
| *C12N 15/67* | (2006.01) |
| *A01H 3/00* | (2006.01) |
| *C12N 15/72* | (2006.01) |
| *C12N 9/22* | (2006.01) |

(52) U.S. Cl.
CPC ............. *A01N 63/02* (2013.01); *A01H 3/00* (2013.01); *A01N 63/00* (2013.01); *C12N 9/22* (2013.01); *C12N 15/67* (2013.01); *C12N 15/72* (2013.01)

(58) Field of Classification Search
CPC .......... C12N 15/67; C12N 15/72; C12N 9/22; A01N 63/02; A01N 63/00; A01H 3/00
USPC ....... 424/93.4, 93.2, 93.1; 435/252.3, 320.1; 536/23.1
See application file for complete search history.

(56) References Cited

U.S. PATENT DOCUMENTS

| | | |
|---|---|---|
| 7,943,819 B2 | 5/2011 | Baum et al. |
| 8,853,489 B2 | 10/2014 | Raemaekers et al. |
| 9,445,603 B2 | 9/2016 | Baum et al. |
| 2013/0130350 A1 | 5/2013 | Chandrasegaran et al. |
| 2014/0259204 A1* | 9/2014 | Schenk .............. C12N 15/8218 800/265 |

FOREIGN PATENT DOCUMENTS

| | | |
|---|---|---|
| EP | 2 530 159 A1 | 12/2012 |
| WO | WO 2012/170433 A1 | 12/2012 |

OTHER PUBLICATIONS

Qi et al., Application of Synechococcus nirA promoter to establish an inducible expression system for engineering the Synechocystis tochopherol pathway. Appl. Environ. Microbiol., 2005, vol. 71 (10): 5678-5684. (Year: 2005).*
Anonymous, "A handbook for high-level expression and purification of 6xHis-tagged proteins," *The QiaExpressionist*, (2003).
Dow et al., "Molecular Genetic Analysis of V-ATPase Function in *Drosophila melanogaster*," *The Journal of Experimental Biology*, 200:237-245 (1997).
Dow, "The multifunctional *Drosophila melanogaster* V-ATPase is encoded by a multigene family," *Journal of Bioenergetics and Biomembranes*, 31:75-83 (1999).
Erdmann et al., "The non-coding RNAs as riboregulators," *Nucleic Acids Research*, 29:189-193 (2001).
Examination Report dated Nov. 14, 2016 in European Patent Application No. 14729497.9.
Examination Report dated May 9, 2017 in European Patent Application No. 14729497.9.
Gottesman, "Micros for microbes: non-coding regulatory RNAs in bacteria," *Trends Genet.*, 21:399-404 (2005).
Griffiths-Jones et al., "Rfam: annotating non-coding RNAs in complete genomes," *Nucleic Acids Research*, 33:D121-D124 (2005).
He et al., "Characterization of an unusual, sequence-specific termination signal for T7 RNA polymerase," *J. Biol. Chem.*, 273(30):18802-18811 (1998).
International Search Report and Written Opinion dated Jul. 24, 2014, in International Application No. PCT/US2014/026036.
Kaps et al., "Energy transfer between fluorescent proteins using a co-expression system in *Mycobacterium smegmatis*, "*Gene*, 278:115-124 (2001).

(Continued)

*Primary Examiner* — Ganapathiram Raghu
(74) *Attorney, Agent, or Firm* — Amanda Carmany-Rampey; David R. Marsh; Arnold & Porter Kaye Scholer LLP

(57) ABSTRACT

Compositions and methods for efficiently producing and delivering double stranded RNA (dsRNA) are provided. Vector constructs useful for in vitro and in vivo expression of dsRNA are described. Also described are cell expression systems for efficient and cost-effective production of dsRNA in living cells and methods and compositions for providing the expressed dsRNA to target organisms. The described compositions and methods can be used to produce RNA molecules for screening or other uses, and to amplify RNA sequences for analysis.

16 Claims, 7 Drawing Sheets

Specification includes a Sequence Listing.

(56) References Cited

OTHER PUBLICATIONS

Lesnik et al., "Prediction of rho-independent transcriptional terminators in *Escherichia coli*," *Nucleic Acids Research*, 29(17):3583-3594 (2001).

Mexican Office Action dated Jul. 11, 2017 in Mexican Patent Application No. MX/a/2015/013118, with English translation.

Qiagen, "The QIAexpressionist™, A handbook for high-level expression and purification of 6xHis-tagged proteins," Fifth Edition, pp. 1 & 15 (2003).

Stead et al., "RNAsnap™: a rapid, quantitative and inexpensive, method for isolating total RNA from bacteria," *Nucleic Acids Research*, 40(20):e156 (2012).

Studier, "Protein production by auto-induction in high density shaking cultures," *Protein Expression and Purification*, 41:207-234 (2005).

Unniraman et al., "Alternate Paradigm for Intrinsic Transcription Termination," *The Journal of Biological Chemistry*, 276(45):41850-41855 (2001).

Unniraman et al., "Conserved economics of transcription termination in eubacteria," *Nucleic Acids Research*, 30 (3), pp. 675-684 (2002).

Wilson et al., "Transcription termination at intrinsic terminators: The role of the RNA hairpin," *Proc. Natl. Acad. Sci. USA*, 92(19):8793-8797 (1995).

\* cited by examiner

Figure 2A

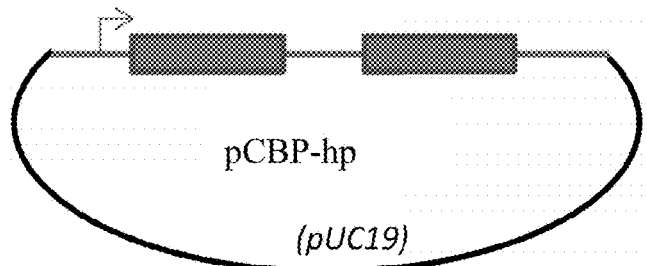

Figure 2B

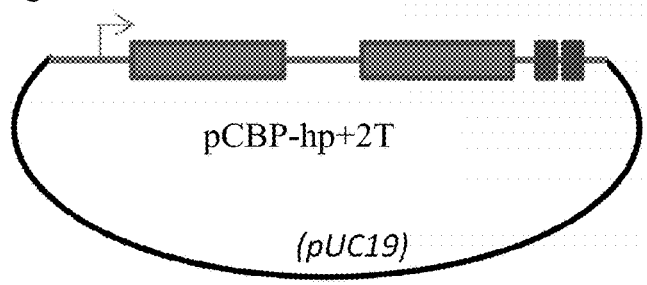

Figure 2C

SEQ ID NO 3

```
T7                        T8593 AS
TAATACGACTCACTATAGGGTACCTGTGGCTCTCACAGGCAGCGAAGATGGTACCGTTAGAGTTTGGCATACGAATACACAGAT
T8593 AS
TAGAGAATTGTTTGAATTATGGGTTCGAGAGAGTGTGGACCATTTGTTGCTTGAAGGGTTCGAATAATGTTTCTCTGGGGTATGAC
T8593 AS
GAGGGCAGTATATTAGTGAAAGTTGGAAGAGAAGAACCGGCAGTTAGTATGGATGCCAGTGGCGGTAAAATAATTTGGGCAAGGCA
T8593 AS                                     Hairpin loop
CTCGGAATTACAACAAGCTAATTTGAAGGCGCTGCCAGAAGGAagtactgcgatcgcgtfaacgcttfatcacgataccttctacc
Hairpin loop
acatatcactaacaacatcaacactcatactctcgacgacatccactcga       tctcacacgaccgattaactctcatcc
Hairpin loop              T8593 S
acgcggccgcctgcagagcCCTTCTGGCAGCGCCTTCAAATTAGCTTGTTGTAATTCCGAGTGCCTTGCCCAAATTATTTTACCG
T8593 S
CCACTGGCATCCATACTAACTGCCGGTTCTTCTCTTCCAACTTTCACTAATATACTGCCCTCGTCATACCCCAGAGAAACATTATT
T8593 S
CGAACCCTTCAAGCAACAAATGGTCCACACTCTCTCGAACCCATAATTCAAACAATTCTCTAATGTGTGTATTCGTATGCCAAA
T8593 S                                     PTH-terminator                pET-T7
CTCTAACGGTACCATCTTCGCTGCCTGTGAGAGCCACAGGTAAgctctgccatatctgttctttgcaagatcagctgagcaataact
pET-T7
agcataaccccttggggcctctaaacgggtcttgaggggttttttgctgaaaggaggaactatatccggaaagaacatgtgagcaa
```

Target Band

-RNAseA

+RNAseA

37°C     51°C     62°C     72°C

4: Marker
5: AIM (auto induction media) *(yield 40mg/L)*
6: super broth + media *(yield 207mg/L)*
7: Plasmid + media *(yield 96mg/L)*

Bacterial DV49 dsRNA

4: Marker
5: super broth + media *(yield 66mg/L)*

Bacterial CPB dsRNA

*In vivo* 'run-off transcription' with T7 RNAP

Advantages:
- Complete termination of transcription
- Defined 5'- and 3'- end of the RNA product
- Transcription from a lineare template vs. supercoiled plasmid

COMPOSITIONS AND METHODS FOR THE PRODUCTION AND DELIVERY OF DOUBLE STRANDED RNA

CROSS REFERENCE TO RELATED APPLICATIONS

This application is a continuation of U.S. application Ser. No. 14/208,788, filed on Mar. 13, 2014, now U.S. Pat. No. 9,445,603, issued on Sep. 20, 2016, which claims the benefit of U.S. Provisional Patent Application No. 61/793,506, filed on Mar. 15, 2013, which is incorporated herein by reference in its entirety.

INCORPORATION OF THE SEQUENCE LISTING

This application contains a sequence listing, submitted herewith electronically via EFS web, containing the file named "P34118US03_SEQ.txt" which is 4,445 bytes in size (measured in MS-Windows®), which was created on Aug. 15, 2016, and which is herein incorporated by reference in its entirety.

FIELD OF THE INVENTION

Vector constructs useful for in vitro and in vivo expression of double-stranded RNA (dsRNA) are provided. Also provided are cell expression systems for producing dsRNA in vivo and methods and compositions for providing in vivo transcripted dsRNA to target organisms.

DESCRIPTION OF THE RELATED ART

Commercial crops are often the targets of attack by viruses or pests such as insects or nematodes. Pest infestation and viral infection can have a significant negative effect on crop yield. Chemical pesticides have been very effective in eradicating pest infestations; however, there are disadvantages to using chemical pesticides. Chemical pesticidal agents are not selective and may exert an effect on beneficial insects and other organisms as well as the targeted pest. Chemical pesticidal agents persist in the environment and generally are slow to be metabolized, if at all. They accumulate in the food chain, and particularly in the higher predator species, where they can assert negative effects. Accumulations of chemical pesticidal agents also results in the development of resistance to the agents. Thus, there is a need for alternative methods for controlling or eradicating insect infestation on or in plants; methods which are selective, environmentally inert, non-persistent, biodegradable, and that fit well into pest resistance management schemes.

Double stranded RNA (dsRNA) molecules have been shown to mediate inhibition of specific, targeted genes in various organisms through a mechanism known as RNA interference (RNAi). RNAi utilizes endogenous cellular pathways whereby a double stranded RNA, which comprises complementary nucleotide sequences that substantially correspond to the sense and anti-sense of a target sequence, mediates the degradation of the mRNA of interest or diminished translation of protein from the mRNA template. The effector proteins of the RNAi pathway include the Dicer protein complex that generates small interfering RNAs (siRNAs) from the original dsRNA and the RNA-induced silencing complex (RISC) that uses siRNA guides to recognize and degrade or block translation from the corresponding mRNAs. Only transcripts complementary to the siRNAs are affected, and thus the knock-down of mRNA expression is usually sequence specific. The gene silencing effect of RNAi can persist for days and, under experimental conditions, can in some cases lead to a decline in abundance of the targeted transcript of 90% or more, with consequent decline in levels of the corresponding protein. Protein levels can also be perturbed by blocking translation without significantly affecting mRNA transcript levels.

While dsRNA molecules show promise as a selective, environmentally inert, alternative to chemical pesticidal agents for controlling or eradicating pest infestation of plants, constraints on the amount of dsRNA that can be produced by traditional in vitro and in vivo expression methods and the costs associated with the production and purification dsRNA present a barrier to its use for controlling pest infestation and disease in crop plants. There is therefore a need for efficient and cost-effective means for producing commercial-scale quantities of dsRNA.

SUMMARY

Several embodiments described herein are related to vector constructs useful for in vitro and in vivo expression of double stranded RNA (dsRNA). Also described are cell expression systems for efficient and cost-effective production of dsRNA in living cells and methods and compositions for providing the expressed dsRNA to target organisms. The described compositions and methods can be used to produce RNA molecules for commercial formulations, to amplify dsRNA sequences for analysis, screening, and other uses.

The present embodiments further relate to compositions and methods for efficiently producing commercial quantities of dsRNA molecules by cell culture and delivering the expressed dsRNA molecules to target organisms. Some embodiments relate to an engineered dsRNA expression construct comprising a promoter; a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript; a first transcription terminator sequence, positioned 3' to the dsRNA encoding region; and a second transcription terminator sequence, positioned 3' to the first transcription terminator, wherein the dsRNA encoding region, first transcription terminator and second transcription terminator are operably linked to the promoter. In some embodiments, the engineered dsRNA expression construct further comprises one or more Zinc finger nuclease (ZFN), TAL-effector nuclease (TALEN) or meganuclease restriction sites positioned 3' to the second transcription terminator sequence. In some embodiments, the meganuclease restriction site is selected from a group consisting of: I-AniI, I-SceI, I-CeuI, PI-PspI, PI-Sce, I-SceIV, I-CsmI, I-PanI, I-PanII, I-PanMI, I-SceII, I PpoI, I-SceIII, I-CreI, I-LtrI, I-GpiI, I-GZeI, I-OnuI, I-Hj eMI, I-MsoI, I-TevI, I-TevII, and I-TevIII. In some embodiments, the engineered dsRNA expression construct further comprises 1, 2, 3, 4, 5, 6, or more additional transcription terminator sequence(s) positioned 3' to the dsRNA encoding region. In some embodiments, the engineered dsRNA expression construct comprises two or more Rho-independent transcription terminator sequences that are each, independently, selected from a group consisting of PTH-terminator, pET-T7 terminator, T3-Tφ terminator, pBR322-P4 terminator, vesicular stomatitis virus terminator, rrnB-T1 terminator, rrnC terminator, and TTadc transcriptional terminator, such that the promoter and transcription terminator sequences form a functional combination. In some embodiments, the transcriptional terminator sequence is a yeast transcriptional terminator sequence. In some embodiments, the engineered dsRNA expression construct comprises one or more Rho-dependent transcription termination signals.

Several embodiments relate to an engineered dsRNA expression construct comprising a promoter; a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript; and a site-specific endonuclease restriction site positioned 3' to the dsRNA encoding region. In some embodiments, the engineered dsRNA expression construct comprises a site-specific endonuclease restriction site chosen from the group consisting of a Zinc finger nuclease (ZFN) restriction site, TAL-effector nuclease (TALEN) restriction site and meganuclease restriction site. In some embodiments, the meganuclease restriction site is selected from a group consisting of: I-AniI, I-SceI, I-CeuI, PI-PspI, PI-Sce, I-SceIV, I-CsmI, I-PanI, I-PanII, I-PanMI, I-SceII, I PpoI, I-SceIII, I-CreI, I-LtrI, I-GpiI, I-GZeI, I-OnuI, I-HjeMI, I-MsoI, I-TevI, I-TevII, and I-TevIII. In some embodiments, the engineered dsRNA expression construct comprises one or more transcription terminator sequences transcriptionally downstream of the dsRNA encoding region and 5' to the site-specific endonuclease restriction site. In some embodiments, the engineered dsRNA expression construct comprises a dsRNA encoding region consisting essentially of SEQ ID NO 2. In some embodiments, the engineered dsRNA expression construct comprises a bacteriophage promoter.

Several embodiments relate to a vector comprising an engineered dsRNA expression construct comprising a promoter; a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript; and a site-specific endonuclease restriction site positioned 3' to the dsRNA encoding region. In some embodiments, the engineered dsRNA expression construct comprises a site-specific endonuclease restriction site chosen from the group consisting of a Zinc finger nuclease (ZFN) restriction site, TAL-effector nuclease (TALEN) restriction site and meganuclease restriction site. In some embodiments, the meganuclease restriction site is selected from a group consisting of: I-AniI, I-SceI, I-CeuI, PI-PspI, PI-Sce, I-SceIV, I-CsmI, I-PanI, I-PanII, I-PanMI, I-SceII, I PpoI, I-SceIII, I-CreI, I-LtrI, I-GpiI, I-GZeI, I-OnuI, I-HjeMI, I-MsoI, I-TevI, I-TevII, and I-TevIII. In some embodiments, the engineered dsRNA expression construct comprises one or more transcription terminator sequences transcriptionally downstream of the dsRNA encoding region and 5' to the site-specific endonuclease restriction site. In some embodiments, the engineered dsRNA expression construct comprises a dsRNA encoding region consisting essentially of SEQ ID NO 2. In some embodiments, the engineered dsRNA expression construct comprises a bacteriophage promoter. In some embodiments, the vector is a plasmid vector.

Several embodiments relate to a vector comprising an engineered dsRNA expression construct comprising a promoter; a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript; a first transcription terminator sequence, positioned 3' to the dsRNA encoding region; and a second transcription terminator sequence, positioned 3' to the first transcription terminator, wherein the dsRNA encoding region, first transcription terminator and second transcription terminator are operably linked to the promoter. In some embodiments, the engineered dsRNA expression construct further comprises one or more Zinc finger nuclease (ZFN), TAL-effector nuclease (TALEN) or meganuclease restriction sites positioned 3' to the second transcription terminator sequence. In some embodiments, the meganuclease restriction site is selected from a group consisting of I-AniI, I-SceI, I-CeuI, PI-PspI, PI-Sce, I-SceIV, I-CsmI, I-PanI, I-PanII, I-PanMI, I-SceII, I PpoI, I-SceIII, I-CreI, I-LtrI, I-GpiI, I-GZeI, I-OnuI, I-Hj eMI, I-MsoI, I-TevI, I-TevII, and I-TevIII. In some embodiments, the engineered dsRNA expression construct further comprises 1, 2, 3, 4, 5, 6, or more additional transcription terminator sequence(s) positioned 3' to the dsRNA encoding region. In some embodiments, the engineered dsRNA expression construct comprises two or more Rho-independent transcription terminator sequences that are each, independently, selected from a group consisting of PTH-terminator, pET-T7 terminator, T3-Tφ terminator, pBR322-P4 terminator, vesicular stomatitus virus terminator, rrnB-T1 terminator, rrnC terminator, and TTadc transcriptional terminator, such that the promoter and transcription terminator sequences form a functional combination. In some embodiments, the vector is a plasmid vector.

Several embodiments relate to a bacterial host cell comprising a vector comprising an engineered dsRNA expression construct comprising a promoter; a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript; and a site-specific endonuclease restriction site positioned 3' to the dsRNA encoding region. Some embodiments relate to a bacterial host cell comprising a vector comprising an engineered dsRNA expression construct comprising a promoter; a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript; a first transcription terminator sequence, positioned 3' to the dsRNA encoding region; and a second transcription terminator sequence, positioned 3' to the first transcription terminator, wherein the dsRNA encoding region, first transcription terminator and second transcription terminator are operably linked to the promoter. In some embodiments, the bacterial host cell does not express RNAse A. In some embodiments, the bacterial host cell is an *E. coli* cell. In some embodiments, the bacterial host cell is dead and un-lysed. In some embodiments, the bacterial host cell may be used in a composition for controlling an invertebrate pest infestation or inhibiting the spread of a viral disease in a population of plants. Several embodiments relate to a method for controlling an invertebrate pest infestation comprising applying a dead and un-lysed bacteria to a plant. In some embodiments, the dead and un-lysed bacteria of any of the embodiments described above is applied to a plant food source for an insect or nematode viral vector in a method for inhibiting the spread of a viral disease in a population of plants.

In some embodiments, a cell culture system for in vivo synthesis of dsRNA comprising a bacterial host cell comprising a vector comprising an engineered dsRNA expression construct comprising a promoter; a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript; and a site-specific endonuclease restriction site positioned 3' to the dsRNA encoding region and a growth media is provided. In some embodiments, a cell culture system for in vivo synthesis of dsRNA comprising a bacterial host cell comprising a vector comprising an engineered dsRNA expression construct comprising a promoter; a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript; a first transcription terminator sequence, positioned 3' to the dsRNA encoding region; and a second transcription terminator sequence, positioned 3' to the first transcription terminator, wherein the dsRNA encoding region, first transcription terminator and second transcription terminator are operably linked to the promoter and a growth media is provided. In some embodiments, the growth media comprises 3.2% Tryptone, 2% Yeast Extract, 0.5% NaCl, 1% glycerol, 0.1% glucose, 0.4% alpha-lactose, 50 mM (NH4)2SO4, 10 mM KH2PO4, 40 mM Na2HPO4, 2 mM MgSO4.

Several embodiments relate to a lysate of a bacterial host cell comprising a vector comprising an engineered dsRNA expression construct comprising a promoter; a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript; and a site-specific endonuclease restriction site positioned 3' to the dsRNA encoding region for controlling an invertebrate pest infestation or inhibiting the spread of a viral disease in a population of plants. Several embodiments relate to a lysate of a bacterial host cell comprising a vector comprising an engineered dsRNA expression construct comprising a promoter; a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript; a first transcription terminator sequence, positioned 3' to the dsRNA encoding region; and a second transcription terminator sequence, positioned 3' to the first transcription terminator, wherein the dsRNA encoding region, first transcription terminator and second transcription terminator are operably linked to the promoter for controlling an invertebrate pest infestation or inhibiting the spread of a viral disease in a population of plants. Several embodiments relate to a method for controlling an invertebrate pest infestation comprising applying a bacterial lysate to a plant. In some embodiments, the bacterial lysate of any of the embodiments described above is applied to a plant food source for an insect or nematode viral vector in a method for inhibiting the spread of a viral disease in a population of plants.

BRIEF DESCRIPTION OF THE DRAWINGS

FIG. 1 consists of FIGS. 1A and 1B.

FIG. 2 consists of FIGS. 2A-2C. FIG. 2A depicts a schematic representation of the pCPB-hp vector.

FIG. 2B depicts a schematic representation of pCPB-hp+2T vector.

FIG. 2C shows a partial map of the pCPB-hp+2T vector.

FIG. 3 consists of FIGS. 3A and 3B.

FIG. 5 consists of FIGS. 5A and 5B.

FIG. 7 consists of FIGS. 7A and 7B.

DETAILED DESCRIPTION

Figure 1A:
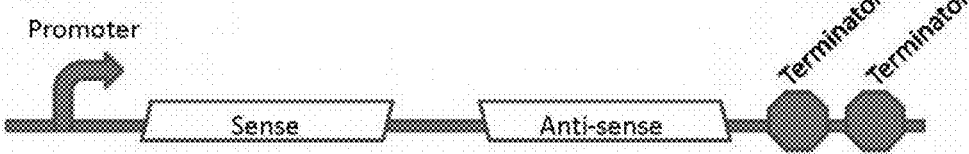
FIG. 1A depicts a schematic representation of an engineered dsRNA expression construct that comprises in a 5' to 3' direction, a promoter operably linked to a sense DNA fragment, a loop encoding region, a complementary anti-sense DNA fragment, a first transcriptional terminator and a second transcriptional terminator.

The following is a detailed description of the invention provided to aid those skilled in the art in practicing the present invention. Those of ordinary skill in the art may make modifications and variations in the embodiments described herein without departing from the spirit or scope of the present invention.

A. Definitions

Unless otherwise defined, all technical and scientific terms used herein have the same meaning as commonly understood by one of ordinary skill in the art. Where a term is provided in the singular, the plural of that term is also contemplated unless otherwise indicated. Unless otherwise stated, nucleic acid sequences in the text of this specification are given in the 5' to 3' direction with respect to the promoter.

In the description that follows, a number of terms are used extensively. The following definitions are provided to facilitate understanding of the present embodiments.

As used herein, "a" or "an" may mean one or more than one.

As used herein, the term "about" indicates that a value includes the inherent variation of error for the method being employed to determine a value, or the variation that exists among experiments.

It will be understood that, although the terms "first," "second," etc. may be used herein to describe various elements, these elements should not be limited by these terms. These terms are only used to distinguish one element from another.

As used herein, the term "nucleic acid" or "nucleic acid molecule" refers a single or double-stranded polymer of deoxyribonucleotide or ribonucleotide bases. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like.

An "isolated nucleic acid molecule" is a nucleic acid molecule that is not integrated in the genomic DNA of an organism. For example, a DNA molecule that encodes a receptor that has been separated from the genomic DNA of a cell is an isolated DNA molecule. Another non-limiting example of an isolated nucleic acid molecule is a chemically-synthesized nucleic acid molecule that is not integrated in the genome of an organism. Another non-limiting example of an isolated nucleic acid molecule is a nucleic acid molecule that has been isolated from a particular species which is smaller than the complete DNA molecule of a chromosome from that species.

The term "vector" refers to a DNA molecule used as a vehicle to artificially carry foreign genetic material into a host cell, where it can be replicated and/or expressed. The DNA sequence of a vector generally comprises an insert (transgene) and a larger sequence that serves as the "backbone." The vector backbone may contain one or more restriction endonuclease recognition sites that allow insertion of a nucleic acid molecule in a determinable fashion without loss of an essential biological function of the vector, nucleotide sequences encoding a marker gene that is suitable for use in the identification and selection of cells transduced with the vector, and an origin of replication. Expression vectors (expression constructs) generally have a promoter sequence that drives expression of the transgene in the host cell. Examples of vectors suitable for use in accordance to the present embodiments include, but are not limited to, plasmids, cosmids, plastomes, artificial chromosomes and bacteriophage.

The terms "promoter" or "promoter sequence" may be used interchangeably and refer to a DNA sequence which when ligated to a nucleotide sequence of interest is capable of controlling the transcription of the nucleotide sequence of interest into RNA. The terms "promoter" and "promoter sequence" include a minimal promoter that is a short DNA sequence comprised of a TATA box and other DNA sequences that serve to specify the site of transcription initiation or are involved in the binding of protein factors which control the effectiveness of transcription initiation in response to physiological conditions. Promoters may be homologous, derived in their entirety from a native gene of the host cell, or heterologous, derived in whole or in part from another organism, or be composed of different elements derived from different promoters found in nature, or be comprised of synthetic DNA segments. As used herein, a promoter may be a constitutively active promoter or a regulated promoter. In some embodiments, the promoter may be repressible. In other embodiments, the promoter may be inducible.

When expression of a nucleotide sequence is placed under the control of a promoter, such nucleotide sequence is said to be "operably linked to" the promoter. Similarly, a regulatory element and a core promoter are "operably linked" if the regulatory element modulates the activity of the core promoter.

The term "host cell" refers to any cell capable of replicating and/or transcribing a vector designed according to the present embodiments. Host cells for use in the present embodiments can be prokaryotic cells, such as E. coli, or eukaryotic cells such as fungi, plant, insect, amphibian, avian or mammalian cells. Insertion of a vector into the target cell is usually called transformation for bacterial cells, transfection for eukaryotic cells, although insertion of a viral vector is often called transduction.

The term "expression" or "gene expression" refers to the biosynthesis of a gene product. For example, in the case of a functional RNA, gene expression involves transcription of the gene into RNA.

As used herein, the phrase "inhibition of gene expression" or "inhibiting expression of a target gene" or "gene suppression" or "suppressing a target gene" refers to the absence (or observable reduction) in the level of protein and/or mRNA product from the target gene.

As used herein, the term "RNA transcript" refers to the product resulting from RNA polymerase-catalyzed transcription of a DNA sequence. When the RNA transcript is a perfect complementary copy of the DNA sequence, it is referred to as the primary transcript or it may be an RNA sequence derived from post-transcriptional processing of the primary transcript and is referred to as the mature RNA.

As used herein, the term "sense RNA" refers to an RNA transcript corresponding to a sequence or segment that, when produced by the target pest, is in the form of a mRNA that is capable of being translated into protein by the target pest cell.

As used herein, the term "anti-sense RNA" refers to an RNA transcript that is complementary to all or a part of a mRNA that is normally produced in a cell of a target pest. The complementarity of an anti-sense RNA may be with any part of the specific gene transcript, i.e., at the 5' non-coding sequence, 3' non-translated sequence, introns, or the coding sequence.

The term "reference sequence" refers to a sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length.

As used herein, the term "target sequence" refers to a nucleotide sequence of a gene targeted for suppression, which corresponds to a duplex-forming region of a dsRNA. In this context, the term "gene" means a locatable region of genomic sequence, corresponding to a unit of inheritance, which includes regulatory regions, transcribed regions, and/or other functional sequence regions. Depending upon the circumstances, the term target sequence can refer to the full-length nucleotide sequence of the gene targeted for suppression or the nucleotide sequence of a portion of a gene targeted for suppression.

A first nucleotide sequence when observed in the 5' to 3' direction is said to be a "complement of", or "complementary to", a second reference nucleotide sequence observed in the 3' to 5' direction if the sequence of the first nucleotide is the reverse complement of the reference nucleotide sequence. For illustration, the nucleotide sequence "CATTAG" corresponds to a reference sequence "CATTAG" and is complementary to a reference sequence "GTAATC." Nucleic acid sequence molecules are said to exhibit "complete complementarity" when every nucleotide of one of the sequences read 5' to 3' is complementary to every nucleotide of the other sequence when read 3' to 5'.

As used herein, "loop" refers to a structure formed by a single strand of a nucleic acid, in which complementary regions that flank a particular single stranded nucleotide region hybridize in a way that the single stranded nucleotide region between the complementary regions is excluded from duplex formation or Watson-Crick base pairing. A loop is a single stranded nucleotide region of any length.

As used herein, the term "sequence identity", "sequence similarity" or "homology" is used to describe sequence relationships between two or more nucleotide sequences. The percentage of "sequence identity" between two sequences is determined by comparing two optimally aligned sequences over a comparison window, such that the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. A sequence that is identical at every position in comparison to a reference sequence is said to be identical to the reference sequence and vice-versa.

As used herein, a "comparison window" refers to a conceptual segment of at least 6 contiguous positions, usually about 50 to about 100, more usually about 100 to about 150, in which a sequence is compared to a reference sequence of the same number of contiguous positions after the two sequences are optimally aligned. The comparison window may comprise additions or deletions (i.e. gaps) of about 20% or less as compared to the reference sequence (which does not comprise additions or deletions) for optimal alignment of the two sequences Those skilled in the art should refer to the detailed methods used for sequence alignment in the Wisconsin Genetics Software Package Release 7.0, Genetics Computer Group, 575 Science Drive Madison, Wis., USA) or refer to Ausubel et al. (1998) for a detailed discussion of sequence analysis.

As used herein, the term "derived from" refers to a specified nucleotide sequence that may be obtained from a particular specified source or species, albeit not necessarily directly from that specified source or species.

The term "endonuclease" or "restriction endonuclease" refers to enzymes that cleave the phosphodiester bond within a polynucleotide chain.

The term "meganuclease" refers to endodeoxyribonucleases characterized by a large recognition site (double-stranded DNA sequences of 12 to 40 base pairs), and which as a result of the size of their recognition site generally occur rarely, if ever, in a given genome. Examples of meganucleases include, but are not limited to, I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-MsoI, I-TevI, I-TevII, and I-TevIII.

The term "TAL effector nuclease" (TALEN) refers to a nuclease comprising a TAL-effector DNA binding domain fused to a nuclease domain. TAL-effector DNA binding domains may be engineered to bind to a desired target and fused to a nuclease domain, such as the Fok1 nuclease domain, to derive a TAL effector domain-nuclease fusion protein.

The term "Zinc-finger nuclease" (ZFN) refers to a nuclease comprising a zinc finger DNA-binding domain fused to a nuclease domain, such as the Fok1 nuclease domain. Zinc finger domains can be engineered to target desired DNA sequences and this enables zinc-finger nucleases to target unique sequences within complex genomes.

The term "cleavage" refers to the breakage of the covalent backbone of a polynucleotide molecule, such as a DNA molecule.

As used herein, the term "pest" refers to insects, arachnids, crustaceans, fungi, bacteria, viruses, nematodes, flatworms, roundworms, pinworms, hookworms, tapeworms, trypanosomes, schistosomes, botflies, fleas, ticks, mites, and lice and the like that are pervasive in the human environment and that may ingest or contact one or more cells, tissues, or fluids produced by a pest host or symbiont.

As used herein, the term "pest resistance" refers to the ability of a pest host, or symbiont to resist attack from a pest that typically is capable of inflicting damage or loss to the pest host or symbiont. As described herein, such pest resistance can be achieved by providing to a surface of a pest host or symbiont a dsRNA molecule comprised in part of a segment of RNA that is identical to a corresponding RNA segment encoded from a DNA sequence within a pest that prefers to feed on the pest host or symbiont. Expression of the gene within the target pest is suppressed by the dsRNA, and the suppression of expression of the gene in the target pest results in the pest host or symbiont being pest resistant.

B. Production of dsRNA

The present disclosure relates to compositions and methods for the efficient and cost-effective production and delivery of a transcribed RNA molecule, which comprises both sense-oriented and anti-sense-oriented segments that form a stabilized, at least partially double-stranded RNA (dsRNA) molecule, capable of suppressing a targeted gene.

dsRNA

Several embodiments described herein relate to vectors and systems for the in vivo or in vitro production of an RNA molecule comprising a first RNA segment linked to a substantially complementary second RNA segment by a third RNA segment. The first and the second RNA segments lie within the length of the RNA molecule and are substantially inverted repeats of each other, such that the complementarity between the first and the second RNA segments results in the ability of the two segments to hybridize in vivo and in vitro to form a double-stranded RNA stem linked together at one end of each of the first and second segments by the third RNA segment, which forms a single-stranded loop. The first and the second segments correspond to the sense and anti-sense, respectively, of a sequence exhibiting substantial identity to a nucleotide sequence targeted for suppression. In some embodiments, the RNA molecule further includes at least a second stem-loop forming region that suppresses at least a second target sequence.

In some embodiments, the length of the sense strand of the RNA duplex can be at least about 10, 15, 20, 25, 30, 35, 40, 45, 50, 55, 60, 65, 70, 75, 80, 90, 100, 110, 120, 130, 140, 150, 160, 170, 180, 190, 200, 250, 300, 350, 400, 450, 500, 550, 600, 650, 700, 750, 800, 900 or more nucleotides. Similarly, in some embodiments, the length of the anti-sense strand of the RNA duplex can be at least about 10, 15, 20, 25, 30, 35, 40, 45, 50, 55, 60, 65, 70, 75, 80, 90, 100, 110, 120, 130, 140, 150, 160, 170, 180, 190, 200, 250, 300, 350, 400, 450, 500, 550, 600, 650, 700, 750, 800, 900 or more nucleotides. The sense and anti-sense strands of the RNA duplex need not be perfectly complementary, and the double-stranded RNA may contain internal non-complementary regions. The sense and anti-sense strands only need to duplex or be substantially complementary to anneal under biological conditions. In some embodiments, when a double-stranded RNA is formed from complementary base pairing of the sense and anti-sense strands, the resulting duplex has blunt ends. In other embodiments, when a double-stranded RNA is formed from complementary base pairing of the sense and anti-sense strands, the dsRNA has an asymmetric structure. In some embodiments, the dsRNA has a 5' overhang of 1, 2, 3, 4, 5, 6, 7, 8, 9, 10, 11, 12, 13, 14, 15 or more nucleotides on the sense strand. In other embodiments, the dsRNA has a 5' overhang of 1, 2, 3, 4, 5, 6, 7, 8, 9, 10, 11, 12, 13, 14, 15 or more nucleotides on the anti-sense strand. In other embodiments, the dsRNA has a 3' overhang of 1, 2, 3, 4, 5, 6, 7, 8, 9, 10, 11, 12, 13, 14, 15 or more nucleotides one the sense strand. In other embodiments, the dsRNA has a 3' overhang of 1, 2, 3, 4, 5, 6, 7, 8, 9, 10, 11, 12, 13, 14, 15 or more nucleotides one the anti-sense strand.

The third RNA segment may comprise any sequence of nucleotides that facilitates or allows the first RNA segment and the second RNA segment to hybridize and form dsRNA. The third RNA segment may comprise a sequence of nucleotides of at least about 1-5 nucleotides in length, 5-10 nucleotides in length, 10-15 nucleotides in length, 15-20 nucleotides in length, 20-25 nucleotides in length, 25-30 nucleotides in length, 30-35 nucleotides in length, 35-40 nucleotides in length, 40-45 nucleotides in length, 45-50 nucleotides in length, 50-55 nucleotides in length, 55-60 nucleotides in length, 60-65 nucleotides in length, 65-70 nucleotides in length, 70-75 nucleotides in length, 75-80 nucleotides in length, 80-85 nucleotides in length, 85-90 nucleotides in length, 90-95 nucleotides in length, 95-100 nucleotides in length, 100-150 nucleotides in length, 150-200 nucleotides in length, 200-250 nucleotides in length, 250-400 nucleotides in length, or at least about 400-500 nucleotides in length. A variety of different sequences can serve as the loop sequence. Examples of specific loop sequences that have been demonstrated to function in shRNAs include UUCAAGAGA, CCACACC, AAGCUU, CTCGAG, CCACC, and UUCG. In some embodiments, the nucleotide sequence of the third RNA segment substantially corresponds to a sense or anti-sense sequence of a segment of the gene targeted for suppression. For example, the third RNA segment may comprise a sequence of nucleotides corresponding to the sense or anti-sense of nucleotides located at a distal end of the gene segment targeted by the self-complementary first and second RNA segments. In other embodiments, the nucleotide sequence of the third RNA segment substantially corresponds to a sense or anti-sense sequence of a segment of a non-targeted gene. In some embodiments, the nucleotide sequence of the third RNA segment is derived from the nucleotide sequence of a loop region of a microRNA (miRNA). In some embodiments, the nucleotide sequence of the third RNA segment is derived from the nucleotide sequence of a loop region of a native microRNA (miRNA) of the targeted organism. In some embodiments, the nucleotide sequence of the third RNA segment is an engineered nucleotide sequence. In some embodiments, the engineered nucleotide sequence of the third RNA segment is derived from a nucleotide sequence of a native gene by altering the GC content. In some embodiments, the nucleotide sequence of the third RNA segment encodes an aptamer.

Any gene may be targeted for suppression by a dsRNA molecule produced according to the present embodiments. Inhibition of a target gene using a dsRNA molecule as described herein is sequence-specific in that nucleotide sequences corresponding to a duplex-forming region of the dsRNA are targeted for RNAi-mediated inhibition. The duplex-forming region of the dsRNA may correspond to the full length nucleotide sequence of the primary transcription product or fully processed mRNA of the target gene or the duplex-forming region of the dsRNA may correspond to a portion of the primary transcription product or fully processed mRNA of the target gene. A nucleotide sequence of a gene targeted for suppression, which corresponds to a duplex-forming region of the dsRNA can be referred to as the "target sequence." The duplex-forming region of the dsRNA may correspond to a portion of a target gene that is at least about 10, 15, 20, 25, 30, 35, 40, 45, 50, 55, 60, 65, 70, 75, 80, 90, 100, 110, 120, 130, 140, 150, 160, 170, 180, 190, 200, 250, 300, 350, 400, 450, 500, 550, 600, 650, 700, 750, 800, 900, or 1,000 nucleotides in length. In some embodiments, duplex-forming region of the dsRNA may correspond to greater than about 20-25 nucleotides of the target gene, greater than about 25-50 nucleotides of the target gene, greater than about 50-75 nucleotides of the target gene, greater than about 75-100 nucleotides of the target gene, greater than about 100-125 nucleotides of the target gene, greater than about 125-150 nucleotides of the target gene, greater than about 150-175 nucleotides of the target gene, or a sequence of greater than about 175-200 nucleotides of the target gene, greater than about 200-250 nucleotides of the target gene, greater than about 250-275 nucleotides of the target gene, greater than about 275-300 nucleotides of the target gene, greater than about 300-325 nucleotides of the target gene, greater than about 325-350 nucleotides of the target gene, greater than about 350-400 nucleotides of the target gene, greater than about 400-450 nucleotides of the target gene, greater than about 450-500 nucleotides of the target gene, greater than about 500-550 nucleotides of the target gene, greater than about 550-600 nucleotides of the target gene, greater than about 600-700 nucleotides of the target gene, or greater than about 700-1,000 nucleotides of the target gene depending on the size of the target gene. The length of the duplex-forming region may be dependent on the length of dsRNA molecules capable of being taken up by the target organism, for example an insect, and the length of dsRNA capable of being processed within a cell of a target organism into fragments that direct RNA interference. The length of the duplex-forming region may also be influenced by the method of dsRNA synthesis.

In some embodiments, a duplex-forming region of a dsRNA molecule has perfect complementarity (100%) to a target sequence. However, absolute sequence identity between the duplex-forming region of a dsRNA molecule and the target sequence is not required. Sequence variations that might be expected due to genetic mutation, strain polymorphism, or evolutionary divergence are tolerated and dsRNA containing a duplex-forming nucleotide sequence with insertions, deletions, and single point mutations relative to the target sequence may be used to inhibit a target gene. The nucleotide sequences of a duplex-forming region of a dsRNA as described herein and the corresponding portion of the target gene may be substantially complementary, for example, the sequences may share at least about 80% identity, at least about 90% identity, at least about 95% identity, at least about 96% identity, at least about 97% identity, at least about 98% identity, or at least about 99% identity, along the sequence being targeted. The duplex-forming region of a dsRNA as described herein may also be defined functionally as a nucleotide sequence that is capable of hybridizing with a portion of the target gene transcript. Increased length may compensate for less homology between a duplex-forming region of a dsRNA molecule and its target sequence. The length of the identical nucleotide sequences may be at least about 15, 16, 17, 18, 19, 20, 21, 22, 23, 24, 25, 26, 27, 28, 29, 30, 35, 40, 45, 50, 60, 70, 80, 90, 100, 200, 300, 400, 500 or at least about 1000 bases.

A duplex-forming region of a dsRNA molecule may be designed against any target sequence, including one or more target sequences selected from a gene native to a pest or pathogen. The target sequence can be selected from a gene native to a eukaryotic organism or a non-eukaryotic organism. A target sequence can include any sequence from any species, including, but not limited to, bacteria; viruses; fungi; plants, including monocots and dicots, such as crop plants, ornamental plants, and non-domesticated or wild plants; invertebrates such as arthropods, annelids, nematodes, and mollusks; and vertebrates such as amphibians, fish, birds, or mammals.

The target sequence can be translatable (coding) sequence, or can be non-coding sequence (such as non-coding regulatory sequence), or both. Non-limiting examples of a non-translatable (non-coding) target sequence include: 5' untranslated regions, promoters, enhancers, or other non-coding transcriptional regions, 3' untranslated regions, terminators, and introns. Target sequences can also include genes encoding microRNAs, small interfering RNAs, RNA components of ribosomes or ribozymes, small nucleolar RNAs, and other non-coding RNAs (see, for example, non-coding RNA sequences provided publicly at rfam.wustl.edu; Erdmann et al. (2001) Nucleic Acids Res., 29:189-193; Gottesman (2005) Trends Genet., 21:399-404; Griffiths-Jones et al. (2005) Nucleic Acids Res., 33:121-124, which are incorporated by reference). Non-limiting examples of a translatable (coding) target sequence include: genes encoding transcription factors, gene encoding receptors, genes encoding hormones, house keeping genes, and genes encoding enzymes involved in the biosynthesis or catabolism of molecules of interest (such as, but not limited to, amino acids, fatty acids and other lipids, sugars and other carbohydrates, biological polymers, and secondary metabolites including alkaloids, terpenoids, polyketides, non-ribosomal peptides, and secondary metabolites of mixed biosynthetic origin). Additionally, target nucleotide sequences may be determined from any plant, insect, viral, bacterial or fungal gene whose function have been established from literature. It is contemplated that several criteria may be employed in the selection of targeted genes. For example, target nucleotide sequences may be determined from genes that play important roles in the viability, growth, development, reproduction and infectivity. These genes may be may be identified by lethal knockout mutations in *Drosophila, C. elegans*, or other organisms. The gene may also be one whose protein product has a rapid turnover rate, so that dsRNA inhibition will result in a rapid decrease in protein levels. In certain embodiments it is advantageous to select a gene for which a small drop in expression level results in deleterious effects for the organism.

In some embodiments, the target sequence is selected from a gene native to an insect. In some embodiments, the target sequence can be selected from a gene native to any insect species that cause damages to the crop plants and subsequent yield losses (an insect pest). Non-limiting examples of insect pests include: corn leaf aphid, fall armyworm, African armyworm, corn earworm, corn leafhopper, corn blotch leaf miner, Western corn rootworm, Northern corn rootworm, Mexican corn rootworm, Southern corn rootworm, cutworm, seedcorn maggot, wireworm, wheat stem maggot, spotted cucumber beetle, green stink bug, brown stink bug, soybean aphid, and soybean stem borer. Genes in the insect may be targeted at the mature (adult), immature (larval), or egg stages. In some embodiments, the gene targeted for suppression, can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis. Where the target sequence is derived from a gene essential to the viability or infectivity of the insect, its down-regulation results in a reduced capability of the insect to survive and infect its host. Hence, such down-regulation results in a "deleterious effect" on the maintenance viability and infectivity of the insect, in that it prevents or reduces the insect's ability to feed off and survive on nutrients derived from the host cells. By virtue of this reduction in the insect's viability and infectivity, resistance and/or enhanced tolerance to infection by an insect is facilitated. In some embodiments, the target sequence is selected from a gene whose protein product has a rapid turnover rate, so that dsRNA inhibition will result in a rapid decrease in protein levels. In certain embodiments it is advantageous to select a gene for which a small drop in expression level results in deleterious effects for the insect.

In some embodiments, the target sequence is selected from a gene that is expressed in the insect gut. In some embodiments, the target sequence is selected from a gene that shares substantial homologies to the nucleotide sequences of known gut-expressed genes that encode protein components of the plasma membrane proton V-ATPase (Dow et al., 1997, J. Exp. Biol., 200:237-245; Dow, Bioenerg. Biomemb., 1999, 31:75-83). This protein complex is the sole energizer of epithelial ion transport and is responsible for alkalinization of the midgut lumen. The V-ATPase is also expressed in the Malpighian tubule, an outgrowth of the insect hindgut that functions in fluid balance and detoxification of foreign compounds in a manner analogous to a kidney organ of a mammal.

In some embodiments, the target sequence is selected from a gene that is involved in the growth, development, and reproduction of an insect. In some embodiments, the target sequence is selected from a gene that encodes CHD3 gene. The CHD3 gene in *Drosophila melanogaster* encodes a protein with ATP-dependent DNA helicase activity that is involved in chromatin assembly/disassembly in the nucleus. Similar sequences have been found in diverse organisms such as *Arabidopsis thaliana, Caenorhabditis elegans*, and *Saccharomyces cerevisiae*. In some embodiments, the target sequence is selected from a gene that encodes β-tubulin gene. The beta-tubulin gene family encodes microtubule-associated proteins that are a constituent of the cellular cytoskeleton. Related sequences are found in such diverse organisms as *Caenorhabditis elegans*, and Manduca Sexta.

In some embodiments, the target sequence can be selected from a gene native to a nematode pest. Non-limiting examples of nematode pests include: Columbia root-knot nematode, Northern root-knot nematode, Southern root-knot nematode, root-knot nematode, false root-knot nematode, corn cyst nematode, soybean cyst nematode, potato cyst nematode, sugar beet cyst nematode, sting nematode, ring nematode, spiral nematode, lance nematode, dagger nematode, needle nematode, lesion nematode, stubby-root nematode, stunt nematode, golden nematode, and potato rot nematode. In some embodiments, the gene targeted for suppression, can encode an essential protein, the predicted function of which is selected from the group consisting of muscle formation, ion regulation and transport, digestive enzyme synthesis, maintenance of cell membrane potential, amino acid biosynthesis, amino acid degradation, sperm formation, development and differentiation, egg formation, digestive enzyme formation, neurotransmission, cell division, energy metabolism, respiration, and apoptosis. Where the target sequence is derived from a gene essential to the viability or infectivity of the nematode, its down-regulation results in a reduced capability of the nematode to survive and infect its host. Hence, such down-regulation results in a "deleterious effect" on the maintenance viability and infectivity of the nematode, in that it prevents or reduces the nematode's ability to feed off and survive on nutrients derived from the host cells. By virtue of this reduction in the nematode's viability and infectivity, resistance and/or enhanced tolerance to infection by a nematode is facilitated. In some embodiments, the target sequence is selected from a gene whose protein product has a rapid turnover rate, so that dsRNA inhibition will result in a rapid decrease in protein levels. In certain embodiments it is advantageous to select a gene for which a small drop in expression level results in deleterious effects for the nematode.

In some embodiments, the target sequence can be selected from a gene native to a fungus. Non-limiting examples of fungi include: *Macrophomina phaseolini, Puccinia sorghi, Ustilago maydis, Exserohilum pedicellatum, Fusarium verticillioides, Fusarium verticillioides,* and *Sphacelotheca reiliana*. In some embodiments, the gene targeted for suppression, can encode an essential protein, the predicted function of which is selected from the group consisting of cell division, energy metabolism, cell wall formation, spore formation, hyphae formation and digestive enzyme synthesis. Where the target sequence is derived from a gene essential to the viability or infectivity of the fungus, its down-regulation results in a reduced capability of the fungus to survive and infect its host. Hence, such down-regulation results in a "deleterious effect" on the maintenance viability and infectivity of the fungus, in that it prevents or reduces the ability of the fungus to feed off and survive on nutrients derived from the host cells. By virtue of this reduction in the viability and infectivity of the fungus, resistance and/or enhanced tolerance to infection by a fungus is facilitated. In some embodiments, the target sequence is selected from a gene whose protein product has a rapid turnover rate, so that dsRNA inhibition will result in a rapid decrease in protein levels. In certain embodiments it is advantageous to select a gene for which a small drop in expression level results in deleterious effects for the fungus.

In certain embodiments, it may be desirable for a dsRNA to inhibit the expression of a targeted gene in more than one species. In some embodiments, it may be desirable to inhibit the expression of a targeted gene in two or more insect species, for example, corn root worm species. In such embodiments, a target sequence may be selected from a gene or a portion of a gene that is highly conserved across the selected species. For example, the target sequence may be selected from a gene or a portion of a gene that has at least about 80% identity, at least about 85% identity, at least about 90% identity, at least about 95% identity, at least about 96% identity, at least about 97% identity, at least about 98% identity, or at least about 99% identity, across the selected species.

In certain embodiments, it may be desirable for a dsRNA to exhibit species-specific activity. In some embodiments, a target sequence may be selected from a native gene or a portion of a native gene from the targeted species that has a low degree of sequence identity with corresponding genes in other species. In some embodiments, the target sequence may be selected from a gene or a portion of a gene where the degree of sequence identity with corresponding genes in other species is less than approximately 80%. In other embodiments, the target sequence may be selected from a gene or a portion of a gene where the degree of sequence identity with corresponding genes in other species is less than approximately 70%. In other embodiments, the target sequence may be selected from a gene or a portion of a gene where the degree of sequence identity with corresponding genes in other species is less than approximately 60%. In certain embodiments, a target sequence is selected from a gene or a portion of a gene that is poorly conserved between individual insect species, or between insects and other organisms. In some embodiments, a target sequence may be selected from a native gene of the targeted species that has no known homologs in other organisms. In some embodiments, a target sequence may be selected from a native gene of the targeted species that has no known homologs in a plant or a vertebrate animal.

Vectors and Expression

Several embodiments described herein relate to an engineered dsRNA expression construct for in vivo and in vitro transcription of dsRNA comprising a promoter operably linked to a dsRNA encoding element. The engineered dsRNA expression constructs described herein may, advantageously, form part of a replicable vector. In the embodiments described herein, efficiency of dsRNA production from the engineered dsRNA expression construct is improved by preventing or minimizing undesired transcription of RNA from the vector backbone. Several ways of preventing or minimizing undesired transcription of the vector backbone are contemplated and may be used independently or in combination. In some embodiments, two or more transcriptional terminator sequences are operably linked to the promoter downstream of the 3' end of the dsRNA encoding element. In some embodiments, one or more restriction sites, which are preferably not found in the host genome, are provided 3' to the dsRNA encoding element. Cleavage at the restriction prevents undesired transcription downstream of the cut site. In some embodiments, a synthetic nucleotide sequence encoding an RNA transcript which can form one or more stem-loop structures through complementary base pairing is operably linked to the promoter downstream of the 3' end of the dsRNA encoding element. In some embodiments, a nucleotide sequence encoding one or more binding sites for a dsDNA-binding protein is provided 3' to the dsRNA encoding element. In some embodiments, the engineered dsRNA expression construct comprises a Rho-dependent termination signal. In some embodiments, the size of the vector backbone is reduced to minimize undesired transcription.

In the embodiments described herein, the engineered dsRNA expression construct comprises a promoter operably linked to a dsRNA encoding element, which comprises: a sense-oriented nucleotide sequence, which is substantially identical to a target sequence; an anti-sense-oriented nucleotide sequence, which is substantially complementary to the sense-oriented nucleotide sequence; and a nucleotide sequence flanked by the complementary sense and anti-sense nucleotide sequences, which encodes one or more nucleotides that are excluded from duplex formation of the complementary regions in the RNA transcript. In some embodiments, the engineered dsRNA expression construct comprises, a promoter operably linked to a dsRNA encoding element, which comprises in a 5' to 3' direction: a sense-oriented nucleotide sequence, which is substantially identical to a target sequence; a nucleotide sequence which encodes a loop-region of a dsRNA molecule; and an anti-sense-oriented nucleotide sequence, which is substantially complementary to the sense-oriented nucleotide sequence. In other embodiments, the engineered dsRNA expression construct comprises, a promoter operably linked to a dsRNA encoding element, which comprises in a 5' to 3' direction: an anti-sense-oriented nucleotide sequence, which is substantially complementary to a target sequence; a nucleotide sequence which encodes a loop-region of a dsRNA molecule; and a sense-oriented nucleotide sequence, which is substantially complementary to the anti-sense-oriented nucleotide sequence. The orientation of the nucleotide sequence encoding a loop-region of a dsRNA molecule may be either sense or anti-sense. In some embodiments, the nucleotide sequence encoding a loop-region of a dsRNA molecule is substantially identical to a portion of a sense or anti-sense sequence of a gene targeted for suppression by the dsRNA molecule. In some embodiments, the nucleotide sequence encoding a loop-region of a dsRNA molecule is substantially identical to a portion of a sense or anti-sense sequence of a gene other than the gene targeted for suppression by the dsRNA molecule. In some embodiments, the nucleotide sequence encoding a loop-region of a dsRNA molecule is an engineered nucleotide sequence. In some embodiments, the nucleotide sequence encoding a loop-region of a dsRNA molecule encodes an aptamer.

In some embodiments, the engineered dsRNA expression construct comprises, a promoter operably linked to a dsRNA encoding element comprising, in a 5' to 3' direction, a sense-oriented nucleotide sequence, which is substantially identical to a nucleotide sequence of at least a portion of a target gene and an anti-sense-oriented nucleotide sequence, which is shorter than the sense-oriented nucleotide sequence and is substantially complementary to the 5' end of the sense-oriented nucleotide sequence. In some embodiments, the engineered dsRNA expression construct comprises, a promoter operably linked to a dsRNA encoding element comprising, in a 5' to 3' direction, a sense-oriented nucleotide sequence, which is substantially identical to a nucleotide sequence of a portion of a target gene and a longer anti-sense-oriented nucleotide sequence, which is substantially complementary to a nucleotide sequence of at least a portion of the target gene, and which comprises on its 3' end a nucleotide sequence which is substantially complementary to the sense-oriented nucleotide sequence. In some embodiments, the engineered dsRNA expression construct comprises, a promoter operably linked to a dsRNA encoding element comprising, in a 5' to 3' direction, an anti-sense-oriented nucleotide sequence, which is substantially complementary to at least a portion of a nucleotide sequence of a target gene and a sense-oriented nucleotide sequence, which is shorter than the anti-sense-oriented nucleotide sequence and which is substantially complementary to the 5' end of the anti-sense-oriented nucleotide sequence. In some embodiments, the engineered dsRNA expression construct comprises, a promoter operably linked to a dsRNA encoding element comprising, in a 5' to 3' direction, an anti-sense-oriented nucleotide sequence, which is substantially complementary to a portion of a nucleotide sequence of a target gene and a longer sense-oriented nucleotide sequence, which is substantially identical to at least a portion of the target gene and comprises on its 3' end a nucleotide sequence which is substantially complementary to the anti-sense-oriented nucleotide sequence.

The promoter used in the engineered dsRNA expression construct may be selected based on the nature of the expression system in which the engineered dsRNA expression construct is expected to function (e.g., a prokaryotic or eukaryotic host cell). The promoter may be a constitutive or inducible promoter. In some embodiments, a bacteriophage promoter, for example the T7, T3, SV40 or SP6, may be used in the engineered dsRNA expression construct, since they provide a high level of transcription which is dependent only on binding of the appropriate RNA polymerase. Where the host cell does not express the appropriate RNA polymerase, a transgene encoding a T7, T3, SV40 or SP6 polymerase operably linked to a host cell-recognized promoter may be provided on the same or a different vector as the engineered dsRNA expression construct. The host cell-recognized promoter may be an inducible promoter or a constitutively active promoter. In some embodiments, a syngenic promoter, which is recognized by polymerases expressed by the host genome, may be used in the engineered dsRNA expression construct. Examples of promoters suitable for use with bacterial hosts include, but are not limited to, T5, β-lactamase promoter, E. coli galactose promoter, arabinose promoter, alkaline phosphatase promoter, tryptophan (trp) promoter, lactose operon (lac) promoter, lacUV5 promoter, trc promoter and tac promoter. In some embodiments, the promoter used in the engineered dsRNA expression construct may be a RNA Pol I, RNA Pol II or RNA Pol III promoter. In certain embodiments, the promoter used in the engineered dsRNA expression construct may be a Pol III promoter. Examples of Pol III promoters include, but are not limited to U6 promoter, tRNA promoter, retroviral LTR promoter, Adenovirus VA1 promoter, 5Sr RNA promoter, 7SK RNA promoter, 7SL RNA promoter, and H1 RNA promoter. In some embodiments, a yeast-recognized promoter, for example the ADR1 promoter, wild-type α-factor promoter or ADH2/GAPD hybrid promoter, may be used in the engineered dsRNA expression construct.

In some embodiments, the engineered dsRNA expression construct may optionally further comprise additional nucleotide sequences that advantageously affect transcription of the dsRNA encoding element and/or the stability of a resulting transcript. For example, the engineered dsRNA expression construct may further comprise one or more enhancer or polyadenylation sequences.

Two principal mechanisms, termed Rho-independent and Rho-dependent termination, mediate transcriptional termination in prokaryotes, such as E. coli. Rho-independent termination signals, such as the transcriptional termination sequences discussed below, do not require an extrinsic transcription-termination factor, as formation of a stem-loop structure in the RNA transcribed from these sequences along with a series of Uridine (U) residues promotes release of the RNA chain from the transcription complex. Rho-dependent termination, on the other hand, requires a transcription-termination factor called Rho and cis-acting elements on the mRNA. The initial binding site for Rho, the Rho utilization (rut) site, is an extended (~70 nucleotides, sometimes 80-100 nucleotides) single-stranded region characterized by a high cytidine/low guanosine content and relatively little secondary structure in the RNA being synthesized, upstream of the actual terminator sequence. When a polymerase pause site is encountered, termination occurs, and the transcript is released by Rho's helicase activity.

Figure 1B:
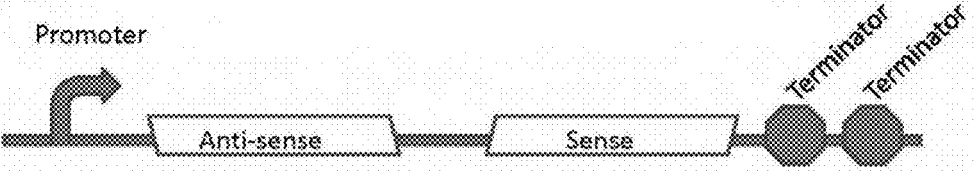
FIG. 1B depicts a schematic representation of an engineered dsRNA expression construct that comprises in a 5' to 3' direction, a promoter operably linked to an anti-sense DNA fragment, a loop encoding region, a complementary sense DNA fragment, a first transcriptional terminator and a second transcriptional terminator.

In some embodiments, the engineered dsRNA expression construct comprises a Rho-dependent termination signal. In some embodiments, the Rho-dependent termination signal is in located in a loop-forming region of the dsRNA transcript. In other embodiments, the Rho-dependent termination signal is in located in a sense or anti-sense sequence of a duplex-forming region of the dsRNA transcript. Nucleic acid sequences encoding Rho-dependent termination signals are known in the art and may also be identified in Rho-dependent terminated genes. In some embodiments, a Rho-dependent termination signal may be provided in conjunction with one or more of a Rho-independent termination sequence, a synthetic nucleotide sequence encoding a stem-loop forming RNA transcript, a binding site for a DNA-binding protein, and a site-specific restriction endonuclease site as described below. An engineered dsRNA expression construct comprising a Rho-dependent termination signal can be expressed in a host cell that expresses Rho transacting factors (a Rho+ cell line). Efficiency of RNA transcription from the engineered dsRNA expression construct can be improved by providing two or more transcriptional termination sequences in tandem at a position 3' to the end of the dsRNA encoding element. See FIG. 1. A transcriptional termination sequence may be any nucleotide sequence, which when placed transcriptionally downstream of a nucleotide sequence encoding an open reading frame, causes the end of transcription of the open reading frame. Such sequences are known in the art and may be of prokaryotic, eukaryotic or phage origin. Examples of terminator sequences include, but are not limited to, PTH-terminator, pET-T7 terminator, T3-Tφ terminator, pBR322-P4 terminator, vesicular stomatitis virus terminator, rrnB-T1 terminator, rrnC terminator, TTadc transcriptional terminator, and yeast-recognized termination sequences, such as Matα (α-factor) transcription terminator, native α-factor transcription termination sequence, ADR1 transcription termination sequence, ADH2 transcription termination sequence, and GAPD transcription termination sequence. A non-exhaustive listing of transcriptional terminator sequences may be found in the iGEM registry, which is available at: partsregistry.org/Terminators/Catalog. The first transcriptional terminator sequence of a series of 2, 3, 4, 5, 6, 7, or more may be placed directly 3' to the final nucleotide of the dsRNA encoding element or at a distance of at least 1-5, 5-10, 10-15, 15-20, 20-25, 25-30, 30-35, 35-40, 40-45, 45-50, 50-100, 100-150, 150-200, 200-300, 300-400, 400-500, 500-1,000 or more nucleotides 3' to the final nucleotide of the dsRNA encoding element. The number of nucleotides between tandem transcriptional terminator sequences may be varied, for example, transcriptional terminator sequences may be separated by 0, 1, 2, 3, 4, 5, 6, 7, 8, 9, 10, 10-15, 15-20, 20-25, 25-30, 30-35, 35-40, 40-45, 45-50 or more nucleotides.

Transcriptional termination sequences may be polymerase-specific or nonspecific, however, transcriptional terminators selected for use in the present embodiments should form a 'functional combination' with the selected promoter, meaning that the terminator sequence should be capable of terminating transcription by the type of RNA polymerase initiating at the promoter. For example, a eukaryotic RNA pol II promoter and eukaryotic RNA pol II terminators, a T7 promoter and T7 terminators, a T3 promoter and T3 terminators, a yeast-recognized promoter and yeast-recognized termination sequences, etc., would generally form a functional combination. The number and identity of the transcriptional termination sequences used may also be selected based on the efficiency with which transcription is terminated from a given promoter. For example, at least 2, 3, 4, 5, 6, 7 or more homologous or heterologous transcriptional terminator sequences may be provided transcriptionally downstream of the dsRNA encoding element to achieve a termination efficiency of at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% from a given promoter.

Several embodiments relate to an engineered dsRNA expression construct comprising a promoter and two or more transcriptional terminators in functional combination for efficient termination of transcription. In some embodiments, a T7 promoter, a PTH-terminator and a pET-T7 terminator form a functional combination. In some embodiments, a T7 promoter, a T5 promoter, a T3 promoter, or a SP6 promoter form a functional combination with one or more Rho-dependent termination signals and one or more Rho-independent termination sequences. In some embodiments, a T7 promoter, a T5 promoter, a T3 promoter, or a SP6 promoter form a functional combination with one or more Rho-dependent termination signals and a TrpR Repressor. In some embodiments, a T7 promoter, a T5 promoter, a T3 promoter, or a SP6 promoter form a functional combination with one or more Rho-independent termination signals and a TrpR Repressor. In some embodiments, a T7 promoter, a T5 promoter, a T3 promoter, or a SP6 promoter form a functional combination with one or more Rho-dependent termination signals and a TyrR Repressor. In some embodiments, a T7 promoter, a T5 promoter, a T3 promoter, or a SP6 promoter form a functional combination with one or more Rho-independent termination signals and a TyrR Repressor. In some embodiments, a T7 promoter, a T5 promoter, a T3 promoter, or a SP6 promoter form a functional combination with one or more Rho-dependent termination signals and a LacI Repressor. In some embodiments, a T7 promoter, a T5 promoter, a T3 promoter, or a SP6 promoter form a functional combination with one or more Rho-independent termination signals and a LacI Repressor. One mechanism of regulating transcription termination, known as intrinsic termination, involves the formation of a hairpin-loop structure in an mRNA strand during transcription, which destabilizes the transcription elongation complex (which involves interactions between the template, transcript and RNA polymerase) and leads to the polymerase becoming dissociated from the DNA template. Accordingly, a synthetic nucleotide sequence may be designed to encode an RNA transcript that forms one or more hairpin loop structures, which promote transcription termination. In several embodiments described herein, efficiency dsRNA transcription is improved by providing a hairpin-encoding synthetic nucleotide sequence transcriptionally downstream of a dsRNA encoding element. Generally, a hairpin can be formed by a palindromic nucleotide sequence that can fold back on itself to form a paired stem region whose arms are connected by a single stranded loop. In some embodiments, the synthetic nucleotide sequence encodes 1, 2, 3, 4, 5, 6, 7, 8, 9, 10 or more RNA hairpins. In some embodiments, the synthetic nucleotide sequence encodes a poly-T sequence 3' to a hairpin-forming palindromic nucleotide sequence. Stability of the hairpin can be correlated with termination efficiency, and hairpin stability is determined by its length, the number of mismatches or bulges it contains and the base composition of the paired region. Pairings between guanine and cytosine have three hydrogen bonds and are more stable compared to adenine-uracil pairings, which have only two. In some embodiments, a stem encoded by the synthetic nucleotide sequence is 4, 5, 6, 7, 8, 9, 10, 11, 12, 13, 14, or 15 base pairs in length. In certain embodiments, a stem encoded by the synthetic nucleotide sequence is 8 or 9 base pairs in length. A loop-forming region may comprise 1, 2, 3, 4, 5, 6, 7, 8, 9, or 10 nucleotides. In some embodiments, the loop-forming region comprises 4-8 nucleotides. In certain embodiments, the loop-forming region comprises 4 nucleotides. The G/C content of a hairpin-forming palindromic nucleotide sequence can be at least 60%, at least 65%, at least 70%, at least 75%, at least 80%, at least 85%, at least 90% or more. In some embodiments, the G/C content of a hairpin-forming palindromic nucleotide sequence is at least 80%. In some embodiments, a synthetic nucleotide sequence encoding 1, 2, 3, 4, 5, 6, 7, 8, 9, 10 or more RNA hairpins may be provided transcriptionally downstream of a dsRNA encoding element in conjunction with one or more transcriptional terminator sequences of prokaryotic, eukaryotic or phage origin. In some embodiments, a nucleotide sequence encoding a series of 4, 5, 6, 7, 8, 9, 10 or more uracils (U) are provided 3' to a hairpin encoding sequence.

Figure 8:
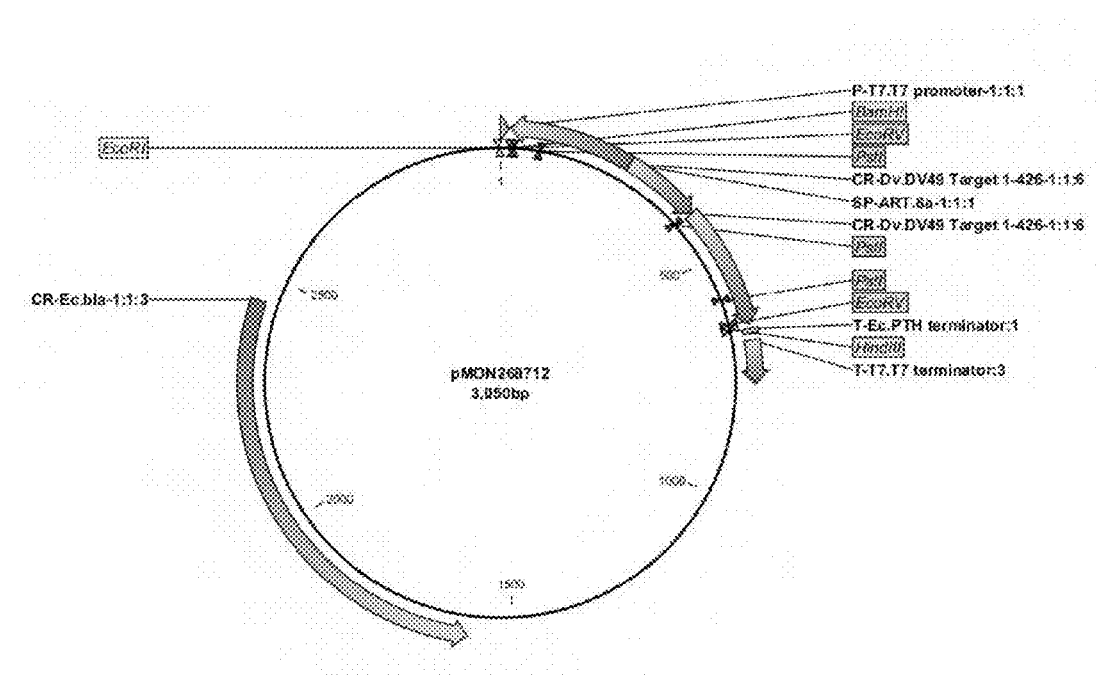
FIG. 8 depicts a schematic representation of pDV49+2T vector.

Pausing of the polymerase during elongation is thought to be an important component of both Rho-dependent and Rho-independent termination. DNA binding proteins can act as road blocks causing the transcription elongation complex to stall, which promotes transcriptional termination. In several embodiments, efficient transcriptional termination is promoted by providing one or more binding sites for a DNA-binding protein 3' to the end of the dsRNA encoding element. In some embodiments, one or more binding sites for a DNA-binding protein are provided proximal to a transcriptional termination sequence, such that termination efficiency is improved. In some embodiments, one or more binding sites for a DNA-binding protein are provided proximal to a synthetic nucleotide sequence which encodes nucleotides that form a hairpin loop. In some embodiments, one or more binding sites for a DNA-binding protein are provided proximal to a Rho-dependent termination site. Any DNA binding protein which, when complexed with DNA, causes pausing of the transcription elongation complex and destabilization of the transcription bubble may be used. For example, one or more binding sites for TrpR repressor, LaI repressor or TyrR repressor may be used. Other examples of DNA binding proteins that can act as transcriptional repressors include PRH, Eve, Krüppel, TGIF, Mad, IRF-2, RP58, E2F-6, MeCP2, and MBD2. Where the host cell does not express an endogenous DNA-binding protein, a nucleotide sequence encoding the DNA-binding protein may be provided on a vector comprising the engineered dsRNA expression construct or it may be provided on a different vector and may expressed under the control of a host cell-recognized promoter or a phage promoter, such as T7, T3 or SP6. In several embodiments, the engineered dsRNA expression construct comprises one or more site-specific endonuclease restriction sites, which are not found in the host cell genome, 3' to the dsRNA encoding element, such that expression of the site-specific endonuclease in a host cell prevents undesired transcription from the engineered dsRNA expression construct downstream of the restriction site by cleaving the engineered dsRNA expression construct without disrupting the host cell genome. See, e.g., FIG. 8. The site-specific endonuclease may be a meganuclease, a zinc finger nuclease (ZFN), or a TAL-effector nuclease (TALEN). Examples of meganucleases include, but are not limited to, I-AniI, I-SceI, I-CeuI, PI-PspI, PI-Sce, I-SceIV, I-CsmI, I-PanI, I-PanII, I-PanMI, I-SceII, I-PpoI, I-SceIII, I-CreI, I-LtrI, I-GpiI, I-GZeI, I-OnuI, I-HjeMI, I-MsoI, I-TevI, I-TevII, and I-TevIII. A nucleotide sequence encoding the site-specific endonuclease may be provided on a vector comprising the engineered dsRNA expression construct or it may be provided on a different vector. In some embodiments, a nucleotide sequence encoding a site-specific endonuclease may be provided on a vector encoding an RNA polymerase, for example, T7, T3, SV40 or SP6 polymerase, and may, optionally, be operably linked to a host cell-recognized promoter. In some embodiments, the engineered dsRNA expression construct comprises one or more site-specific endonuclease cleavage sites 3' to one or more termination sequences. In some embodiments, the engineered dsRNA expression construct comprises one or more ZFN restriction sites, TALEN restriction sites or meganuclease restriction sites selected from the group consisting of I-AniI, I-SceI, I-CeuI, PI-PspI, PI-Sce, I-SceIV, I-CsmI, I-PanI, I-PanII, I-PanMI, I-PpoI, I-SceIII, I-CreI, I-LtrI, I-GpiI, I-GZeI, I-OnuI, I-HjeMI, I-MsoI, I-TevI, I-TevII, and I-TevIII, 3' to one or more transcription termination sequences selected from the group consisting of PTH-terminator, pET-T7 terminator, T3-Tφ terminator, pBR322-P4 terminator, vesicular stomatitis virus terminator, rrnB-T1 terminator, rrnC terminator, TTadc transcriptional terminator, Matα (α-factor) transcription terminator, native α-factor transcription termination sequence, ADR1 transcription termination sequence, ADH2 transcription termination sequence, and GAPD transcription termination sequence.

Engineered RNA expression constructs as described herein, such as those set forth at SEQ ID NOs:2 and 4, may be constructed from component sequence elements and incorporated into a suitable vector using standard recombinant DNA techniques well known in the art. Many vectors are available for this purpose, and selection of the appropriate vector will depend mainly on the size of the nucleic acid to be inserted into the vector and the particular host cell to be transformed with the vector. Examples of vectors suitable for use in accordance to the present embodiments include, but are not limited to, plasmids, cosmids, plastomes, bacterial artificial chromosomes, yeast artificial chromosomes and bacteriophage. The vector backbone may contain various components depending on the vector's function (amplification of DNA or expression of DNA) and the particular host cell with which it is compatible. For example, the vector backbone may contain one or more restriction endonuclease recognition sites that allow insertion of a nucleic acid molecule in a determinable fashion without loss of an essential biological function of the vector, nucleotide sequences encoding a selectable marker, such as such as an antibiotic resistance gene, that is suitable for use in the identification and selection of cells transduced with the vector, a promoter sequence that drives expression of the transgene in the host cell, and an origin of replication. Examples of available bacterial vectors include, but are not limited to, pUC19, pUC18, pBluescript, pGEM, pACYC184 and pBR322 vectors.

In some embodiments, the size of the vector backbone is minimized to reduce the amount of template available for undesired transcription. In some embodiments, a minimal vector suitable for use in accordance with the present embodiments does not comprise one or more protein-based selectable markers, such as antibiotic resistance markers, nonessential spacer and junk sequences that do not encode a defined function. In some embodiments, a minimal vector suitable for use in accordance with the present embodiments consists essentially of a multiple cloning site, a selectable marker gene and an origin of replication. A minimal vector suitable for use in accordance with the present embodiments may be less than 3 kb. In some embodiments, the vector is less than 2.7 kb. In some embodiments, the vector is less than 2.6 kb. In some embodiments, the vector is less than 2.5 kb. In some embodiments, the vector is less than 2.4 kb. In some embodiments, the vector is less than 2.3 kb. In some embodiments, the vector is less than 2.2 kb. In some embodiments, the vector is less than 2.1 kb. In some embodiments, the vector is less than 2.0 kb. In some embodiments, the vector is less than 1.9 kb. In some embodiments, one or more engineered dsRNA expression constructs and/or one or more dsRNA encoding elements are cloned into the minimal vector to achieve a minimum size of at least 3 kb.

The dsRNA molecules encoded by the engineered dsRNA expression constructs described herein may be synthesized in vitro or in vivo in a host cell. Endogenous RNA polymerase of the host cell may mediate transcription in vivo, or cloned RNA polymerase, such as, bacteriophage RNA polymerase (e.g., T3, T7, SV40, SP6), can be used for transcription in vivo or in vitro.

One or more vectors comprising an engineered dsRNA expression construct as described above may be introduced into a wide variety of prokaryotic and eukaryotic microorganism hosts to produce the stabilized dsRNA molecules. Several embodiments described herein relate to a host cell that expresses dsRNA from an engineered dsRNA expression construct designed to minimize unproductive transcription of non-functional sequence. Suitable host cells include, but are not limited to, fungi, filamentous fungi, yeast, algae and bacteria. To prevent degradation of the dsRNA molecules transcribed in the host cell, an RNAse III deficient host may be used.

In some embodiments, the host cell is a eukaryotic cell. Suitable eukaryotic host cells include, but are not limited to, fungal cells, algal cells, insect cells, and plant cells. Suitable fungal host cells include, but are not limited to, yeast cells and filamentous fungal cells.

In one embodiment, the fungal host cell is a yeast. In one embodiment, the yeast is from one of the genera: *Candida, Hansenula, Saccharomyces, Schizosaccharomyces, Pichia, Kluyveromyces,* and *Yarrowia*. In some embodiments, the yeast cell is *Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans,* or *Yarrowia lipolytica*.

In other embodiments, the host cell is a prokaryotic cell. Suitable prokaryotic cells include gram positive, gram negative and gram-variable bacterial cells. Suitable prokaryotic host cells include, but are not limited to, species of: *Agrobacterium, Alicyclobacillus, Anabaena, Anacystis, Acinetobacter Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmun, Streptomyces, Streptococcus, Synnecoccus, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* and *Zymomonas*. In some embodiments, the bacterial host cell is non-pathogenic to humans.

In some embodiments, the bacterial host cell is of the *Bacillus* species, e.g., *B. thuringiensis, B. megaterium, B. subtilis, B. lentus, B. circulans, B. pumilus, B. lautus, B. coagulans, B. brevis, B. licheniformis, B. clausii, B. stearothermophilus* and *B. amyloliquefaciens*. In some embodiments, the bacterial host cell is of the *Clostridium* species, e.g., *C. acetobutylicum, C. tetani* E88, *C. lituseburense, C. saccharobutylicum, C. perfringens,* and *C. beijerinckii*. In some embodiments, the bacterial host cell is of the *Corynebacterium* species e.g., *C. glutamicum* and *C. acetoacidophilum*. In some embodiments, the bacterial host cell is of the *Escherichia* species, e.g., *E. coli*. In some embodiments, the bacterial host cell is an RNAse III deficient *E. coli* strain, for example *E. coli* HT115 (DE3). In some embodiments the bacterial host cell is of the *Erwinia* species, e.g., *E. uredovora, E. carotovora, E. ananas, E. herbicola, E. punctata,* and *E. terreus*. In some embodiments, the bacterial host cell is of the *Pantoea* species, e.g., *P. citrea* and *P. agglomerans*. In some embodiments, the bacterial host cell is of the *Pseudomonas* species, e.g., *P. pudita, P. mevalonii,* and P. sp. D-0110. In some embodiments, the bacterial host cell is of the *Streptococcus* species, e.g., *S. equisimiles, S. pyogenes,* and *S. uberis*. In some embodiments, the bacterial host cell is of the *Streptomyces* species, e.g., *S. ambofaciens, S. avermitilis, S. coelicolor, S. aureofaciens, S. aureus, S. fungicidicus, S. griseus,* and *S. lividans*. In some embodiments, the bacterial host cell is of the *Zymomonas* species, e.g., *Z. mobilis* and *Z. lipolytica*.

In some embodiments, microorganisms, such as bacteria, algae, and fungi, known to inhabit the phylloplane (the surface of the plant leaves) and/or the rhizosphere (the soil surrounding plant roots) of a wide variety of important crops may be desirable host cells for the production and delivery of the dsRNA. To prevent degradation of the dsRNA molecules transcribed in the host microorganisms, an RNAse III deficient host may be used. Of particular interest are microorganisms, such as bacteria, e.g., genera *Bacillus* (including the species and subspecies *B. thuringiensis* kurstaki HD-1, *B. thuringiensis* kurstaki HD-73, *B. thuringiensis* sotto, *B. thuringiensis* berliner, *B. thuringiensis thuringiensis, B. thuringiensis tolworthi, B. thuringiensis dendrolimus, B. thuringiensis alesti, B. thuringiensis galleriae, B. thuringiensis aizawai, B. thuringiensis* subtoxicus, *B. thuringiensis entomocidus, B. thuringiensis tenebrionis* and *B. thuringiensis* san diego); *Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc,* and *Alcaligenes*; fungi, particularly yeast, e.g., genera *Saccharomyces, Cryptococcus, Kluyveromyces, Sporobolomyces, Rhodotorula,* and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodobacter sphaeroides, Xanthomonas campestris, Rhizobium melioti, Alcaligenes eutrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium* pollulans.

Several embodiments relate to a cell expression system for producing dsRNA with improved transcriptional efficiency from an engineered dsRNA expression construct designed to minimize unproductive transcription of non-functional sequence. In one aspect, a method of producing dsRNA by culturing host cells which comprise an engineered dsRNA expression construct as described herein is provided. In some embodiments, the host cell expresses dsRNA from an engineered dsRNA expression construct of SEQ ID NO: 2. In other embodiments, the host cell expresses dsRNA from an engineered dsRNA expression construct of SEQ ID NO: 4. In some embodiments, the host cell is a bacterial cell, for example an *E. coli* cell, which is RNAse III deficient.

Methods of employing recombinant DNA technologies to prepare a recombinant DNA construct and vector encoding stabilized dsRNA molecules, and to transform and generate host cells that transcribe the stabilized dsRNA molecules are readily available in the art.

C. Application of dsRNA

Several embodiments relate to compositions and methods for delivering dsRNA transcribed from an engineered dsRNA expression construct designed to minimize unproductive transcription of non-functional sequence as described above to a target organism. In some embodiments, the dsRNA is synthesized in vitro from the engineered dsRNA expression construct and provided to the target organism. In other embodiments, the dsRNA provided to the target organism is transcribed in a host cell (in vivo) from the engineered dsRNA expression construct.

Certain embodiments relate to a method of delivering dsRNA to a target organism comprising expressing the dsRNA from an engineered dsRNA expression construct as described above in a host cell and providing the host-cell-transcribed dsRNA to the target organism. In some embodiments, the host-cell-transcribed dsRNA is isolated from the host cell and purified before being provided to the target organism. For example, dsRNA can be purified from a host cell lysate by extraction with a solvent or resin, precipitation, electrophoresis, chromatography, or a combination thereof. Alternatively, the dsRNA may be used with minimal or no purification. For example, in some embodiments, a host cell comprising dsRNA transcribed from an engineered dsRNA expression construct or a lysate prepared from the dsRNA-expressing host cell is provided to the target organism. In some embodiments, the dsRNA suppresses an essential gene of the target organism. In other embodiments, the dsRNA suppresses an essential gene of a pest or pathogen of the target organism. For example, the dsRNA can suppress a viral gene.

As described above, a host cell, such as a bacteria or yeast, can be engineered to produce dsRNA from an engineered dsRNA expression construct as described herein. These host cells can be eaten by an insect pest or other targeted organism. When taken up, the dsRNA can initiate an RNAi response, leading to the degradation of the target mRNA and where the target mRNA encodes an essential protein, weakening or killing of the feeding organism. As shown in Example 3, feeding in vitro transcribed dsRNA molecules comprising Colorado Potato Beetle (CPB) RNA sequences, bacterially transcribed dsRNA molecules comprising CBP RNA sequences, or bacteria expressing dsRNA comprising CPB RNA sequences transcribed from an engineered dsRNA expression construct to CPB larvae all result in the death or inhibition of development and differentiation of the larvae that ingest the dsRNA compositions. All CPB dsRNA preparations showed significant activity against CPB larvae, with the lowest concentration (0.00002 mg/mL) of the CPB dsRNA-expressing bacteria preparation inhibiting 87.5% of CPB growths. Activity of the dsRNA-expressing bacteria in inhibiting the growth and development of the target organism indicates that host cells engineered to efficiently express dsRNA as described herein may be provided directly to a target organism, for example by feeding, to suppress the activity of a target gene without the need for additional RNA purification steps.

The host cell, which in many applications is bacterial, yeast or algal cell, preferably should be killed before being provided to a target organism or a food source of a target organism. For example, where a dsRNA-expressing bacteria is being used as a biological pesticide, or another application where an engineered dsRNA-expressing host cell is used in an environment where contact with humans or other mammals is likely. The dsRNA-expressing host cells may be killed by any means that does not result in significant degradation of the dsRNA. For example, host cells may be killed by heat treatment, by chemical treatment, for example, phenol or formaldehyde treatment, or by mechanical disruption. In some embodiments, host cells are killed without significant lysis. In some embodiments, host cells, for example, bacterial cells, are heated to a temperature sufficient to kill the cells without causing lysis. For example, host cells can be heated to a temperature of at least 59° C., 60° C., 61° C., 62° C., 63° C., 64° C., 65° C., 66° C., 67° C., 68° C., 69° C., 70° C., 71° C., 72° C., 73° C., 74° C., or at least 75° C.

In some embodiments, the engineered dsRNA-expressing host cell is lysed and the cell lysate is provided to a target organism or a food source of a target organism. The dsRNA-expressing host cells may be lysed by any means that does not result in significant degradation of the dsRNA. For example, host cells may be lysed by freeze-thawing, by treatment with a chemical, for example a detergent, toluene, or sodium hydroxide, by enzymatic treatment or by mechanical disruption, for example by homogenization. In some embodiments, the crude lysate is provided to a target organism or a food source of a target organism. In other embodiments, a partially purified lysate or isolated host-cell-expressed dsRNA is provided to a target organism or a food source of a target organism.

Another embodiment relates to methods and compositions for preventing or inhibiting a viral disease in target organism, for example, a mammal, a bird, an arthropod, or a fish. Specific examples of target organisms include but are not limited to, pigs, cows, bison, horses, goats, chicken, quail, ducks, geese, turkey, shrimp, prawns, lobster, crab, honey bees, salmon, tilapia, seabass, carp and catfish. In one embodiment, a dsRNA comprising a nucleotide sequence which is complementary to at least a part of an RNA transcript of a viral gene is administered to a target organism, such that expression of the targeted viral gene is silenced. In one embodiment, an anti-viral dsRNA composition is incorporated in a food source or is applied to the surface of a food source, for example, a crop plant, for consumption by a target organism. In one aspect, the anti-viral dsRNA composition comprises dsRNA molecules transcribed from an engineered dsRNA expression construct designed to minimize unproductive transcription of non-functional sequence as described above. In another aspect, the anti-viral dsRNA composition comprises killed dsRNA-expressing host cells as described above or a lysate thereof. In some embodiments, an unlysed, heat-killed bacterial cell comprising an engineered dsRNA expression construct designed to minimize unproductive transcription of non-functional sequence as described above is fed to a target organism selected from the group consisting of mammals, birds, arthropods, or fish. In one embodiment, the target organism is a shrimp or prawn and the engineered dsRNA expression construct encodes a dsRNA comprising a nucleotide sequence which is complementary to at least a part of an RNA transcript of a gene of White spot syndrome virus, *Monodon* baculovirus, Baculoviral midgut gland necrosis virus, Haematopoietic necrosis virus, Yellow head virus, Taura syndrome virus, Infectious myonecrosis virus, *Macrobrachium rosenbergii* nodavirus, Laem-Singh virus or Mourilyan virus. In one embodiment, the target organism is a fish and the engineered dsRNA expression construct encodes a dsRNA comprising a nucleotide sequence which is complementary to at least a part of an RNA transcript of a gene of Epizootic haematopoietic necrosis virus, Red sea bream iridovirus, Koi herpesvirus, Infectious haematopoietic necrosis virus, Viral haemorrhagic septicaemia virus, Spring viraemia of carp virus, Infectious salmon anaemia virus, or Viral nervous necrosis virus.

Several embodiments relate to compositions and methods for controlling invertebrate pest infestations. In some embodiments, a delivery system for the delivery of dsRNA pesticidal compositions to invertebrate pests through their exposure to a diet containing the dsRNA pesticidal compositions is provided. In one embodiment, dsRNA pesticidal compositions are incorporated in a food source of the pest or applied to the surface of a pest food source, for example, a crop plant, for consumption by an invertebrate pest. In one aspect, the dsRNA pesticidal compositions comprise purified dsRNA molecules transcribed from an engineered dsRNA expression construct designed to minimize unproductive transcription of non-functional sequence as described above. In another aspect, the dsRNA pesticidal compositions comprise unlysed, killed dsRNA-expressing host cells as described above. In another aspect, the dsRNA pesticidal compositions comprise the unpurified or minimally purified lysate of dsRNA-expressing host cells as described above. The compositions may, in addition to the dsRNA, host cells or lysate, contain further excipients, diluents or carriers.

Another embodiment relates to methods and compositions for inhibiting the spread of a viral disease in a population of plants, for example, crop plants. Plant viruses are generally transmitted to a plant by an arthropod or nematode vector. Thus, infection of a plant by a virus can be inhibited by suppressing viral gene expression in the arthropod or nematode vector. Compositions and methods for inhibiting viral gene expression in an arthropod or nematode vector are thus provided. One embodiment relates to a method comprising administering a dsRNA, wherein the dsRNA comprises a nucleotide sequence which is complementary to at least a part of an RNA transcript of a gene from the plant virus, to an arthropod or nematode vector, such that expression of the targeted viral gene is silenced. The targeted RNA transcript may be from an Abutilon mosaic virus, African cassava mosaic virus, Alfalfa mosaic virus, Arabis mosaic virus, Barley mild mosaic virus, Barley yellow dwarf virus, Barley yellow mosaic virus, Beet curly top virus, Beet western yellows virus, Bean golden mosaic virus, Beet leaf curl virus, Beet necrotic yellow vein virus, Beet soil-borne virus, Beet western yellow virus, Brome mosaic virus, Cassava mosaic begomovirus, Cauliflower mosaic virus, Cucumber mosaic virus, Cucumber necrosis virus, Cucurbit aphid-borne yellows virus, Cacao swollen shoot virus, Grapevine fanleaf virus, Grapevine leafroll-associated viruses, Grapevine virus A, Grapevine virus B, Groundnut ringspot virus, Iris yellow spot virus, Johnson grass mosaic virus, Lettuce infectious yellow virus, Lettuce mosaic virus, Pea early browning virus, Pepper ringspot virus, Potato leafroll virus, Potato mop top virus, Rice dwarf virus, Rice ragged stunt virus, Soil-borne wheat mosaic virus, Southern bean mosaic virus, Strawberry latent ringspot virus, Sweetpotato feathery mottle virus, Tobacco mosaic virus, Tobacco rattle virus, Tobacco ringspot virus, Tomato black ring virus, Tomato chlorotic spot virus, Tomato golden mosaic virus, Tomato yellow leaf curl virus, Tomato spotted wilt virus, Velvet tobacco mosaic virus, or a Wheat streak mosaic virus. In one embodiment, an anti-viral dsRNA composition is incorporated in a food source or applied to the surface of a food source, for example, a crop plant, for consumption by a viral vector. In one aspect, the anti-viral dsRNA composition comprises purified dsRNA molecules transcribed from an engineered dsRNA expression construct designed to minimize unproductive transcription of non-functional sequence as described above. In another aspect, the anti-viral dsRNA composition comprises unlysed, killed dsRNA-expressing host cells as described above. In another aspect, the anti-viral dsRNA composition comprises the unpurified or minimally purified lysate of dsRNA-expressing host cells as described above. The arthropod vector may be an insect vector, for example, aphids, beetles, planthoppers, leafhoppers, mealybugs, mirids, mites, thrips, and whiteflies. The compositions may, in addition to the dsRNA, host cells or lysate, contain further excipients, diluents or carriers. Compositions comprising a dsRNA-expressing heat-killed microorganism or a lysate thereof should be sufficiently stable such that the dsRNA remains un-degraded and capable of mediating RNAi even when exposed to external environmental conditions for a length of time, which may be a period of days or weeks.

In the embodiments described herein, dsRNA may be expressed by microorganisms comprising an engineered dsRNA expression construct designed to minimize unproductive transcription of non-functional sequence as described above and the microorganisms or a lysate thereof may be applied onto a surface of a plant or seed or introduced into a seed, root, stem or leaf by a physical means, such as an injection, or in the cases of a seed by imbibition. For example, delivery of microorganisms comprising an engineered dsRNA expression construct as described herein to the surfaces of a plant may be via a spray-on application. In one embodiment, a bacterium or yeast engineered to produce and accumulate dsRNAs may be cultured and the products of the culture, such as heat-killed bacterium or yeast or a lysate thereof, may be formulated as a composition compatible with common agricultural practices. The nature of any excipients and the physical form of the composition may vary depending upon the nature of the substrate treated. For example, the composition may be a liquid that is brushed or sprayed onto or imprinted into the substrate to be treated, or a coating or powder that is applied to the substrate to be treated. Thus, in one embodiment, the composition is in the form of a coating on a suitable surface which adheres to, and is eventually ingested by a target organism, such as an insect or nematode, which comes into contact with the coating.

Spray-on formulations for crop plants may include appropriate stickers and wetters for efficient foliar coverage as well as UV protectants to protect dsRNAs from UV damage. For example, it might be desirable to have a formulation of a heat killed microorganism that would help disperse the microorganism into a film on the leaf surface, or move the heat killed microorganism into the intercellular spaces of the leaf, and/or that would provide some ability for the microorganism to adhere to the leaf under wet environmental conditions (rain-fast-ness). Such additives are commonly used in the bioinsecticide industry and are well known to those skilled in the art. Likewise, formulations for soil application may include granular formulations that serve as a bait for larvae of soil insect pests such as the corn rootworm. Such applications could be combined with other insecticide applications, biologically based or not, to enhance plant protection from insect feeding damage. For example, when *Bacillus thuringiensis* (Bt) proteins are provided in the diet of insect pests a mode of action for controlling the insect pest. Thus, several embodiments relate to synergistic combinations of the dsRNA compositions and methods described herein with Bt methods and compositions, which include topical formulations and transgenic approaches for controlling insect infestation.

Examples of plants to which the methods and compositions described herein may be applied include, but are not limited to, alfalfa, aneth, apple, apricot, artichoke, arugula, asparagus, avocado, banana, barley, beans, beet, blackberry, blueberry, broccoli, brussel sprouts, cabbage, canola, cantaloupe, carrot, cassava, cauliflower, celery, cherry, cilantro, citrus, clementine, coffee, corn, cotton, cucumber, Douglas fir, eggplant, endive, escarole, *eucalyptus*, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, *papaya*, parsley, pea, peach, peanut, pear, pepper, persimmon, pine, pineapple, plantain, plum, pomegranate, poplar, potato, pumpkin, quince, *radiata* pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The methods and compositions described herein may be applied to any monocot or dicot plant, or may be applied to through pharmaceutically acceptable formulations to vertebrate or invertebrate animals in order to provide some level of reduction of target gene expression. Inhibition of target gene expression may be quantified by measuring either the endogenous target RNA or the protein produced by translation of the target RNA and the consequences of inhibition can be confirmed by examination of the outward phenotype of the targeted cell or organism. Techniques for quantifying RNA and proteins are well known to one of ordinary skill in the art. In some embodiments, target gene expression is inhibited by at least 10%, by at least 33%, by at least 50%, or by at least 80%. In some embodiments, target gene expression is inhibited by at least 90%, by at least 95%, or by at least 99% within the cells of the targeted organism so a significant inhibition takes place. Significant inhibition can be said to occur where administration of a dsRNA to a targeted organism results in a detectable phenotype (e.g., cessation of larval growth, paralysis or mortality, etc.) or a detectable decrease in endogenous RNA and/or protein corresponding to the target gene. While in some embodiments, inhibition occurs in substantially all cells of the targeted organism, in some embodiments, inhibition can occur in only a subset of cells expressing the gene. For example, if the targeted gene plays an essential role in cells of an insect alimentary tract, inhibition of the targeted gene within these cells is sufficient to exert a desired deleterious effect on the insect.

The following Examples are presented for the purposes of illustration and should not be construed as limitations.

Example 1

Design of dsRNA Production Vector

A target sequence, nucleotides 30-309 of SEQ ID NO 1, was selected from the putative Colorado Potato Beetle (CPB) ortholog of COPI coatomer.

```
SEQ ID NO 1:
>Ld_F38E11.5 putative COPI coatomer ortholog;
Alias Ld248; 14810:1..379

CGTAACCGCGGTTTGTTTCCACCCTGAACTACCTGTGGCTCTCACAGGC

AGCGAAGATGGTACCGTTAGAGTTTGGCATACGAATACACACAGATTAG

AGAATTGTTTGAATTATGGGTTCGAGAGAGTGTGGACCATTTGTTGCTT

GAAGGGTTCGAATAATGTTTCTCTGGGGTATGACGAGGGCAGTATATTA
```
-continued
```
GTGAAAGTTGGAAGAGAAGAACCGGCAGTTAGTATGGATGCCAGTGGCG

GTAAAATAATTTGGGCAAGGCACTCGGAATTACAACAAGCTAATTTGAA

GGCGCTGCCAGAAGGTGGAGAAATAAGAGATGGGGAGCGTTTACCTGTC

TCTGTAAAAGATATGGGAGCATGTGAAATATACCCT
```

A dsRNA encoding element was designed containing a sense sequence (nucleotides 4-283 of SEQ ID NO 2), which corresponds to the CPB COPI coatomer target sequence, a 150 nucleotide loop-encoding sequence (nucleotides 284-433 of SEQ ID NO 2), and an anti-sense sequence (nucleotides 434-713 of SEQ ID NO 2) which is the reverse complement of the CPB COPI coatomer target sequence.

```
SEQ ID NO 2
GGGTACCTGTGGCTCTCACAGGCAGCGAAGATGGTACCGTTAGAGTTTG

GCATACGAATACACACAGATTAGAGAATTGTTTGAATTATGGGTTCGAG

AGAGTGTGGACCATTTGTTGCTTGAAGGGTTCGAATAATGTTTCTCTGG

GGTATGACGAGGGCAGTATATTAGTGAAAGTTGGAAGAGAAGAACCGGC

AGTTAGTATGGATGCCAGTGGCGGTAAAATAATTTGGGCAAGGCACTCG

GAATTACAACAAGCTAATTTGAAGGCGCTGCCAGAAGGaagtactgcga tcgcgttaacgctttatcacgatacCttctaccacatatcactaacaac atcaacactcatcactctcgacgacatccactcgatcactactctcaca cgaccgattaactcctcatccacgcggccgcctgcaggagcCCTTCTGG

CAGCGCCTTCAAATTAGCTTGTTGTAATTCCGAGTGCCTTGCCCAAATT

ATTTTACCGCCACTGGCATCCATACTAACTGCCGGTTCTTCTCTTCCAA

CTTTCACTAATATACTGCCCTCGTCATACCCCAGAGAAACATTATTCGA

ACCCTTCAAGCAACAAATGGTCCACACTCTCTCGAACCCATAATTCAAA

CAATTCTCTAATCTGTGTGTATTCGTATGCCAAACTCTAACGGTACCAT

CTTCGCTGCCTGTGAGAGCCACAGGTA
```

Two plasmid vectors for producing CPB dsRNA were constructed using the pUC19 cloning vector, which contains an ampicillin resistance gene, an N-terminal fragment of the *E. coli* lac Z gene, a multiple cloning site and an origin of replication. The CPB-hp vector was constructed such that a T7 promoter is operably linked to the dsRNA encoding region of SEQ ID NO 2. See FIG. 2A, which shows a schematic map of the pCPB-hp vector. To prevent or minimize read-through of non-dsRNA encoding regions by T7 RNA polymerase and the production of useless ssRNA from the plasmid backbone, pCPB-hp+2T vector was constructed by placing two T7 terminator sequences (PTH-terminator and pET-T7 terminator) at the 3' end of the dsRNA encoding region. See FIGS. 2B and 2C, which shows schematic maps of the pCPB-hp+2T vector.

*E. coli* strain HT115 (DE3) was purchased from the *Caenorhabditis* Genetics Center, University of Minnesota (the genotype of HT115 (DE3) is: F-, mcrA, mcrB, IN(rrnD-rrnE)1, rnc14::Tn10(DE3 lysogen: lavUV5 promoter-T7 polymerase) (RNAse III minus)). *E. coli* HT115 (DE3) cells were transformed with pUC19 (control), pCPB-hp, or pCPB-hp+2T and grown overnight at 37° C. or 25° C. Total RNA was isolated from 20 ul of culture and was either run directly on an Agarose gel (FIG. 3A, lanes marked 1 (pUC19), 2 (pCPB-hp), and 3 (pCPB-hp+2T)) or treated with RNAse before being run on an Agarose gel (FIG. 3B lanes marked 1 (pUC19), 2 (pCPB-hp), and 3 (pCPB-hp+2T)).

E. coli HT115 (DE3) cells were also transformed with two plasmids, one carrying a dsRNA template (pUC19(control), pCPB-hp, or pCPB-hp+2T) and the other carrying T7 RNA polymerase under the control of an inducible element (IPTG-inducible T7 polymerase). The transformed cells were grown overnight at 37° C. or 25° C. Total RNA was isolated from 20 ul of culture and was either run directly on an Agarose gel (FIG. 3A, lanes marked 4 (pUC19 & pLac-T7), 5 (pCPB-hp & pLac-T7), and 6 (pCPB-hp+2T & pLac-T7)) or treated with RNAse before being run on an Agarose gel (FIG. 3B lanes marked 4 (pUC19 & pLac-T7), 5 (pCPB-hp & pLac-T7), and 6 (pCPB-hp+2T & pLac-T7)).

Figure 3A:
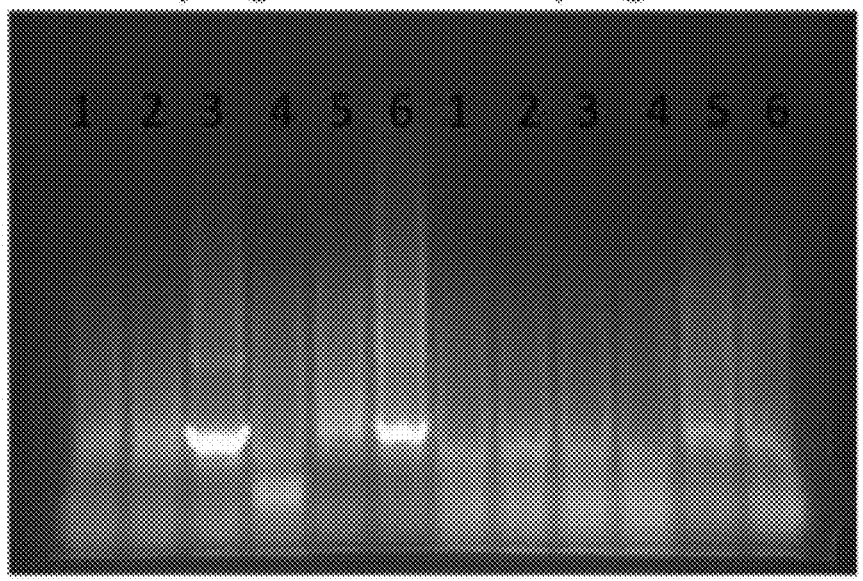
FIG. 3A is a photograph of an Agarose gel showing total RNA isolated from 20 uL of culture grown overnight at 37° C. (Left Lanes) or 25° C. (Right Lanes). Lanes marked with a "1" show total RNA isolated from pUC19/HT115(DE3) bacteria. Lanes marked with a "2" show total RNA isolated from pCPB-hp/HT115(DE3) bacteria. Lanes marked with a "3" show total RNA isolated from pCPB-hp+2T/HT115(DE3) bacteria. Lanes marked with a "4" show total RNA isolated from pUC19/HT115(DE3)+pLac-T7 bacteria. Lanes marked with a "5" show total RNA isolated from pCPB-hp/HT115 (DE3)+pLac-T7 bacteria. Lanes marked with a "6" show total RNA isolated from pCPB-hp+2T/HT115(DE3)+pLac-T7 bacteria.
Figure 3B:
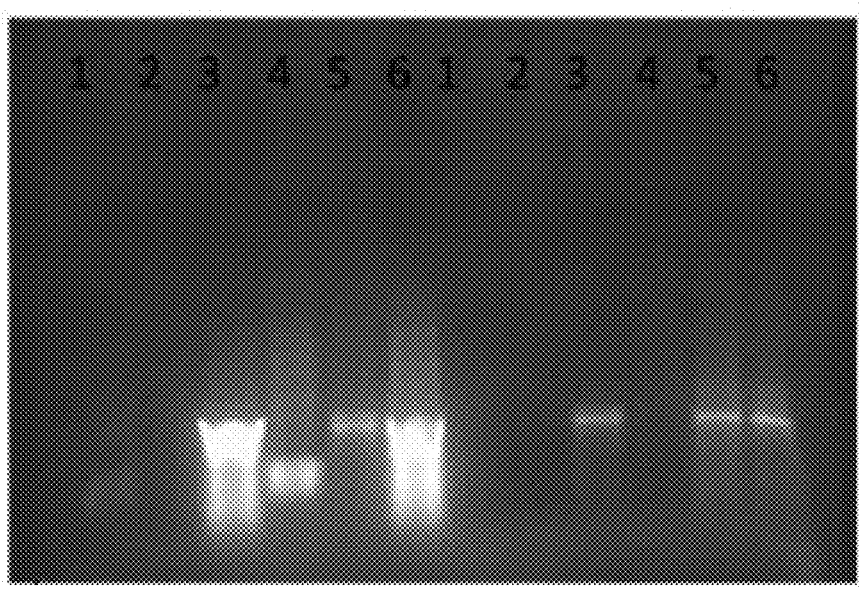
FIG. 3B is a photograph of an Agarose gel showing RNAse A treated total RNA isolated from 20 uL of culture grown overnight at 37° C. (Left Lanes) or 25° C. (Right Lanes). Lanes marked with a "1" show total RNA isolated from pUC19/HT115(DE3) bacteria. Lanes marked with a "2" show total RNA isolated from pCPB-hp/HT115(DE3) bacteria. Lanes marked with a "3" show total RNA isolated from pCPB-hp+2T/HT115(DE3) bacteria. Lanes marked with a "4" show total RNA isolated from pUC19/HT115 (DE3)+pLac-T7 bacteria. Lanes marked with a "5" show total RNA isolated from pCPB-hp/HT115(DE3)+pLac-T7 bacteria. Lanes marked with a "6" show total RNA isolated from pCPB-hp+2T/HT115(DE3)+pLac-T7 bacteria.

As shown in FIG. 3A and FIG. 3B, transformed cells grown at 37° C. produced more RNA than cells grown at 25° C., the yield of dsRNA was improved by the expression of T7 polymerase in the host cells, and the inclusion of two terminator sequences 3' to the dsRNA template resulted in further increases in dsRNA yield. A yield of 30-50 mg/L dsRNA was observed from E. coli cells expressing T7 RNA polymerase and the pCPB-hp+2T dsRNA construct. (Data not shown.)

Example 2

In Vivo Production of Colorado Potato Beatle (CPB) dsRNA

1. Transformation

The pCPB-hp+2T & pLac-T7 plasmids were transformed into E. coli strain HT115 (DE3) as described in Example 1. Following transformation the E. coli cells were plated and single colonies were selected.

2. Culture Condition

Single colonies were grown 6-8 hours at 37° C. in 3 ml LB medium containing 100 ug/ml ampicillin and 12.5 ug/ml tetracycline to produce a seed culture. To induce expression of dsRNA, 200 ul of the seed culture was inoculated into a 250 ml flask with 50 ml auto induction media (AIM) (Studier, Protein Expression and Purification 41 (2005) 207-234) containing 100 ug/ml ampicillin and 12.5 ug/ml tetracycline and then incubated. The cells were harvested by centrifugation at 6000 g for 10 min at 4° C.

3. RNA Purification

Bacterial RNA was purified using a method adapted from Stead's SNAP protocol (Stead et al, Nucleic Acids Res. 2012 Nov. 1; 40 (20):e156.) with modification to the RNA extraction buffer as described below. One milliliter of bacterial culture (~$10^8$ cells) was centrifuged at 16,000 g for 30 s and the supernatant was removed. The cell pellet was stored in dry ice until ready for extraction. Cell pellets were then resuspended in 100 μl of modified RNA extraction solution [18 mM EDTA, 0.025% SDS, 5 mM TCEP, 95% formamide (RNA grade)] by vortexing vigorously. The 1% 2-mercaptoethanol utilized in the RNA extraction solution of Stead's SNAP protocol was replaced with 5 mM TCEP because TCEP has much lower toxicity compared with 2-mercaptoethanol and equal efficacy with 2-mercaptoethanol (data not shown).

Following resuspension in modified RNA extraction solution, the cells were lysed by incubating the sample at 95° C. in a water bath for 7 min. The cell debris were pelleted by centrifuging the warm sample at 16,000 g for 5 min at room temperature. The supernatant was carefully transferred to a fresh tube without disturbing the pellet.

Figure 4:
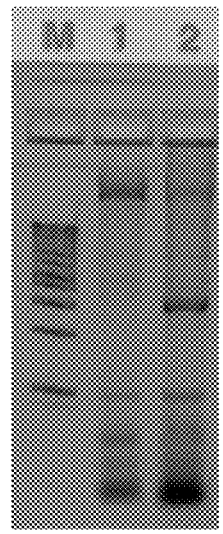
FIG. 4 is a photograph of an Agarose gel showing total bacterial RNA without induction in lane 1 and total bacterial RNA with induction in lane 2. M: marker.

Total RNA isolated from non-induced (FIG. 4, lane 1) and induced (FIG. 4, lane 2) pCPB-hp+2T E. Coli cells was diluted with H2O and run on an Agarose gel. As shown in FIG. 4, a band corresponding to CPB dsRNA was observed in induced pCPB-hp+2T E. Coli cells but not non-induced pCPB-hp+2T E. Coli cells.

Example 3

Comparison of In Vivo and In Vitro Transcribed RNA

Figure 5A:
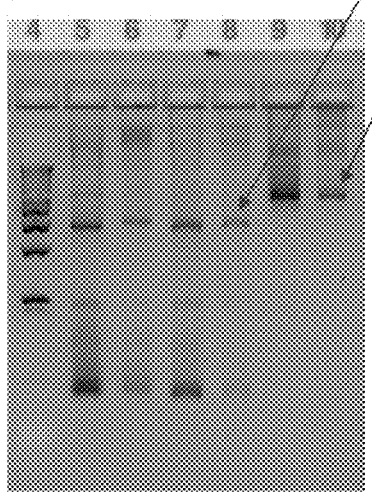
FIG. 5A is a photograph of an Agarose gel showing bacterially transcribed RNA (lanes 5-8) and in vitro transcribed RNA (lanes 9 and 10) without RNAse A digestion. Lane 4 shows a size marker. Lane 5 shows a 10 fold dilution of modified-SNAP purified RNA. Lane 6 shows a 50 fold dilution of modified-SNAP purified RNA. Lane 7 shows a 10 fold dilution of 30 K spin-filtered modified-SNAP purified RNA. Lane 8 shows a 50 fold dilution of 30 K spin-filtered modified-SNAP purified RNA. Lane 9 shows a 100 fold dilution of RNA transcribed in vitro from linearized pCPB-hp+2T vector. Lane 10 shows a 500 fold dilution of RNA transcribed in vitro from linearized pCPB-hp+2T vector.

The pCPB-hp+2T plasmid was linearized and used as template for in vitro transcription of RNA. In vitro transcribed RNA (FIG. 5A, lanes 9 and 10) was run on an Agarose gel along with bacterially transcribed RNA purified according to the modified-SNAP protocol described in Example 1 and diluted directly in H2O (FIG. 5A, lanes 5 and 6) or filtered with a 30K molecular cut membrane (Amicon) to remove reagents such as EDTA, SDS, TCEP and formamide, before diluting with H2O (FIG. 5A, lanes 5 and 6) to determine size of the RNA transcripts. The in vitro transcripted RNA was observed to be larger than the bacterially transcribed RNA (See FIG. 5A).

Figure 5B:
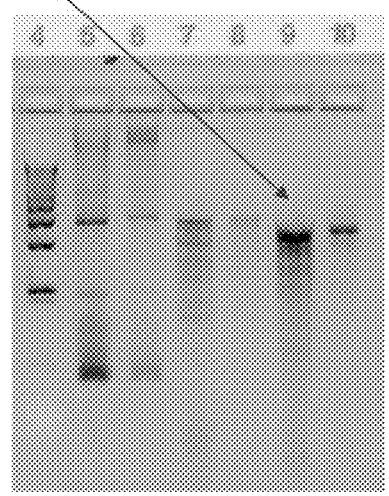
FIG. 5B is a photograph of an Agarose gel showing the results of RNAse A digestion of bacterially transcribed RNA (lanes 5-8) and in vitro transcribed RNA (lanes 9 and 10). Lane 4 shows a size marker. Lane 5 shows a 10 fold dilution of modified-SNAP purified RNA. Lane 6 shows a 50 fold dilution of modified-SNAP purified RNA. Lane 7 shows a 10 fold dilution of 30 K spin-filtered modified-SNAP purified RNA. Lane 8 shows a 50 fold dilution of 30 K spin-filtered modified-SNAP purified RNA. Lane 9 shows a 100 fold dilution of RNA transcribed in vitro from linearized pCPB-hp+2T vector. Lane 10 shows a 500 fold dilution of RNA transcribed in vitro from linearized pCPB-hp+2T vector.

The in vitro and in vivo (bacterially) transcripted RNA was incubated with RNAse A, which digests single stranded but not double stranded RNA. As shown in FIG. 5B, following RNAse A digestion, the size of in vivo (lanes 5-8) and in vitro (lanes 9 and 10) RNA transcription products are identical. This indicated that the increased size of in vitro transcripted RNA was due to the presence of the single-stranded hairpin loop; which is removed in the bacterial cell by RNA processing.

Example 4

Heat-Killing of E. coli

Figure 6:
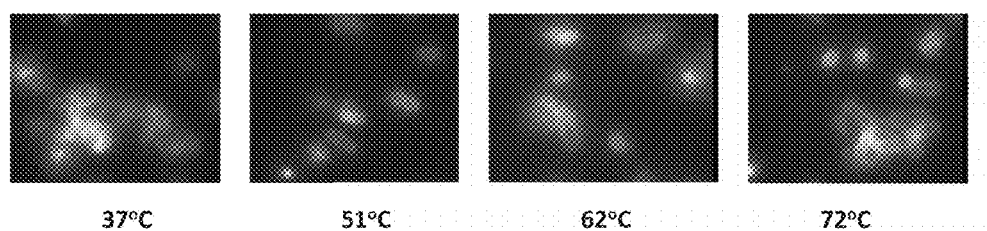
FIG. 6 shows micrographs of *E. coli* cells following incubation at 37, 51, 62 or 72° C. for 30 minutes.

The temperature range for heat-killing E. coli HT115 (DE3) cells without cell lysis was experimentally determined. E. coli HT115 (DE3) cells were incubated at different temperature from 37° C. to 72° C. for 30 mins. The heat-treated cells were then examined under microscope to determine if lysis had occurred and spread on LB plates and incubated overnight to determine survivability after heat treatment. As shown Table 1, heating to temperatures of 59° C. and higher killed all cells, yet cell lysis was not observed for any of the temperatures tested, up to 72° C. (See FIG. 6).

TABLE 1

| Cell Lysis and Survivability Following Heat Treatment | | | | | | | |
|---|---|---|---|---|---|---|---|
|  | 37° C. | 51° C. | 54° C. | 59° C. | 62° C. | 67° C. | 69° C. |
| Low OD Cell lysis (Microscope) | − | − | − | − | − | − | − |

TABLE 1-continued

Cell Lysis and Survivability Following Heat Treatment

|  | 37° C. | 51° C. | 54° C. | 59° C. | 62° C. | 67° C. | 69° C. |
|---|---|---|---|---|---|---|---|
| Low OD Cell survive (LB plate) | + | + | − | − | − | − | − |
| High OD Cell lysis (Microscope) | − | − | − | − | − | − | − |
| High OD Cell survive (LB plate) | + | + | <10% | − | − | − | − |

All cells were treated for 30 minutes at different temperature. Low OD is $OD_{600}$"0.2 and High OD is $OD_{600}$"2.

Example 5

Optimizing Bacterial dsRNA Yield—Growth Media

Three rich media, Auto Induction Media (AIM) (Studier, Protein Expression and Purification 41 (2005) 207-234), Super Broth (Atlas, R. M. Handbook of microbiological media. 1997. *CRC Press*, New York, USA)+media, and Plasmid+ AIM media, were tested to determine if the yield of bacterial RNA production could be improved by media choice.

Auto Induction Media (AIM) contains: 1% N—Z-amine AS, 0.5% yeast extract, 0.5% glycerol, 0.05% glucose, 0.2% alpha-lactose, 25 mM (NH4)2SO4, 5 mM KH2PO4, 20 mM Na2HPO4, 1 mM MgSO4.

Super Broth+ AIM media contains: 3.2% Tryptone, 2% Yeast Extract, 0.5% NaCl, 1% glycerol, 0.1% glucose, 0.4% alpha-lactose, 50 mM (NH4)2SO4, 10 mM KH2PO4, 40 mM Na2HPO4, 2 mM MgSO4.

Plasmid+ AIM media contains: Plasmid+ media (Thomson Instrument Co.), 25 mM (NH4)2SO4, 5 mM KH2PO4, 20 mM Na2HPO4, 1 mM MgSO4, 0.5% glycerol, 0.05% glucose, 0.2% alpha-lactose for auto induction.

Seed cultures of DV49 *E. coli* HT115 (DE3) cells were prepared according to the culture conditions described in Example 2. The 3 different production media were inoculated with identical amounts of seed culture and incubated according to the conditions described in Example 2. After 16 hours of flask culture, the cells were harvested for yield test.

Figure 7A:
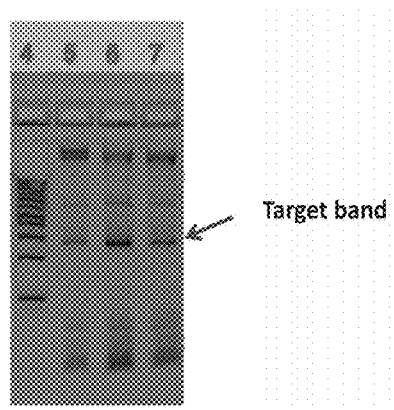
FIG. 7A is a photograph of an Agarose gel showing total RNA isolated from pDV49 bacteria grown in Auto Induction Media (AIM) (Lane 5), Super Broth+ AIM media (Lane 6), or Plasmid+ AIM media (Lane 7). Lane 4 shows a size marker. The DV49 dsRNA bands are indicated by the arrow.

DV49 cells grown in AIM yielded 40 mg/L RNA. DV49 cells grown in Super Broth+media yielded 207 mg/L RNA. DV49 cells grown in Plasmid+ AIM media yielded 96 mg/L RNA. Based on the yield of bacterial DV49 RNA from 3 medium, Super broth+ gave the highest yield of target product. See FIG. 7A.

Figure 7B:
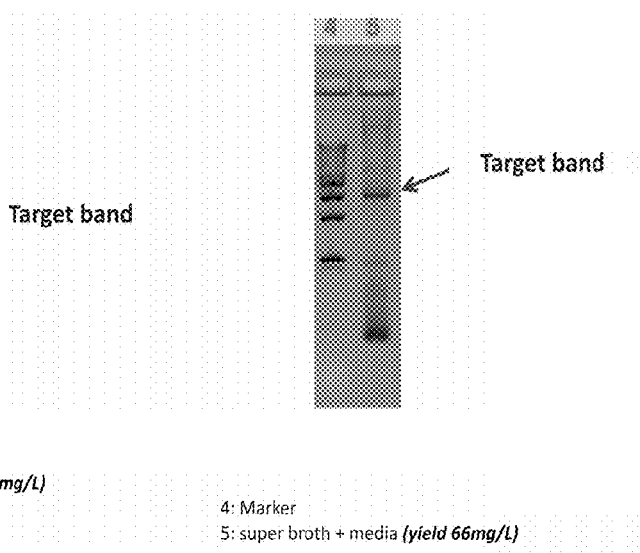
FIG. 7B is a photograph of an Agarose gel showing total RNA isolated from pCPB-hp+2T bacteria grown in Super Broth+media (Lane 5). Lane 4 shows a size marker. The CPB dsRNA band is indicated by the arrow.

The effect of Super broth+ media on CPB dsRNA production was tested as described above. pCPB-hp+2T *E. coli* HT115 (DE3) cells cultured in Super broth+ media yielded 66 mg/L RNA. See FIG. 7B. The yield in Super broth+ media is an improvement over other media tested.

Example 6

Bioefficacy of dsRNA on Colorado Potato Beetle

Three dsRNA samples, unlysed heat-killed pCPB-hp+2T *E. coli* HT115 (DE3), purified bacterially transcribed CBP dsRNA, and in vitro transcribed CBP dsRNA, were produced as described above to test the bioefficacy of the dsRNA preparations against Colorado potato beetle (CPB), *Leptinotarsa decemlineata*.

Bioassays with the CPB larvae were conducted using an artificial diet of 13.2 g/L agar (Serva 11393), 140.3 g/L Bio-Serve pre-mix (F9380B), 5 ml/L KOH (18.3% w/w), and 1.25 ml/L formalin (37%). The diet was dispensed in 200 uL aliquots into 96-well plates and dried briefly prior to sample application. Twenty (20) uL aliquots of test sample (unlysed heat-killed pCPB-hp+2T *E. coli* HT115 (DE3), purified bacterially transcribed CBP dsRNA, or in vitro transcribed CBP dsRNA) were applied per well, with sterile water serving as the untreated control (UTC). Plates were allowed to dry before larvae were added. One neonate CPB larva was added per well with a fine paintbrush. The plates were then sealed with mylar and ventilated using an insect pin. Thirty-two larvae (32) were tested per treatment.

The bioassay plates were incubated at 27° C., 60% relative humidity (RH), in complete darkness for 10-12 days. The plates were then scored for mortality (Table 2) and larval stunting (Table 3). Data was analyzed using JMP©4 statistical software (SAS Institute, 1995) and a full factorial ANOVA was conducted with a Dunnet's test to look for treatment effects compared to the untreated control (P<0.05). A Tukey-Kramer post hoc test was performed to compare all pairs of the treatments (P<0.05).

As shown in Tables 2 and 3, all CPB dsRNA preparations showed significant activity against Colorado potato beetle. For example, 87.5% of beetle growths were inhibited at the lowest concentration of unlysed heat-killed *E. coli* tested (0.00002 mg/ml).

TABLE 2

CPB dsRNA Mortality Bioassay

| Treatment String | dsRNA Conc (mg/mL) | Mean | Std Dev | SEM | P > \|t\| (Neg) | T Grouping | Contamination |
|---|---|---|---|---|---|---|---|
| *E. coli* HeatTmt{60 C.; 30 min} | 0.00002 | 87.50 | 10.21 | 5.10 | *** | A | 0 |

TABLE 2-continued

CPB dsRNA Mortality Bioassay

| Treatment String | dsRNA Conc (mg/mL) | Mean | Std Dev | SEM | P > \|t\| (Neg) | T Grouping | Contamination |
|---|---|---|---|---|---|---|---|
| E. coli HeatTmt{60 C.; 30 min} | 0.0001 | 100.00 | 0.00 | 0.00 | *** | A | 0 |
| E. coli HeatTmt{60 C.; 30 min} | 0.0005 | 100.00 | 0.00 | 0.00 | *** | A | 0 |
| bacterial dsRNA | 0.00002 | 62.50 | 10.21 | 5.10 | *** | B | 0 |
| bacterial dsRNA | 0.0001 | 93.75 | 12.50 | 6.25 | *** | A | 0 |
| bacterial dsRNA | 0.0005 | 100.00 | 0.00 | 0.00 | *** | A | 0 |
| in vitro trancripted dsRNA | 0.00002 | 43.75 | 21.65 | 10.83 | *** | C | 0 |
| in vitro trancripted dsRNA | 0.0001 | 93.30 | 7.77 | 3.88 | *** | A | 0 |
| in vitro trancripted dsRNA | 0.0005 | 96.88 | 6.25 | 3.13 | *** | A | 0 |
| dH20 | 0 | 6.25 | 7.22 | 3.61 | | D | 0 |
| non-induced E. coli HeatTmt{60 C.; 30 min} | 0 | 9.38 | 18.75 | 9.38 | | D | 0 |

TABLE 3

CPB dsRNA Stunting Bioassay

| Treatment String | Conc (mg/mL) | Mean | Std Dev | SEM | P > \|t\| (Neg) | T Grouping | Contamination |
|---|---|---|---|---|---|---|---|
| E. coli HeatTmt{60 C.; 30 min} | 0.00002 | 2.33 | 1.15 | 0.67 | *** | AB | 0 |
| E. coli HeatTmt{60 C.; 30 min} | 0.0001 | . | | | | | 0 |
| E. coli HeatTmt{60 C.; 30 min} | 0.0005 | . | | | | | 0 |
| bacterial dsRNA | 0.00002 | 0.25 | 0.50 | 0.25 | | D | 0 |
| bacterial dsRNA | 0.0001 | 1.00 | | | | CD | 0 |
| bacterial dsRNA | 0.0005 | . | | | | | 0 |
| in vitro trancripted dsRNA | 0.00002 | 1.75 | 0.50 | 0.25 | *** | BC | 0 |
| in vitro trancripted dsRNA | 0.0001 | 3.00 | 0.00 | 0.00 | *** | A | 0 |
| in vitro trancripted dsRNA | 0.0005 | 2.00 | | | *** | ABC | 0 |
| dH20 | 0 | 0.00 | 0.00 | 0.00 | | D | 0 |
| non-induced E. coli HeatTmt{60 C.; 30 min} | 0 | 0.00 | 0.00 | 0.00 | | D | 0 |

Example 7

Bioefficacy of DV49 dsRNA

A pUC backboned plasmid with a T7 promoter driving the expression of anti-sense DV49+loop+sense DV49+PTH-terminator+pET-T7 terminator was constructed. See FIG. 8. The nucleotide sequence of the DV49 expression construct is provided in SEQ ID NO. 4.

```
SEQ ID NO 4:
TAATACGACTCACTATAGGGATCCATGATATCGTGAACATCATCTACAT

TCAAATTCTTATGAGCTTTCTTAAGGGCATCTGCAGCATTTTTCATAGA

ATCTAATACAGCAGTATTTGTGCTAGCTCCTTCGAGGGCTTCCCTCTGC

ATTTCAATAGTTGTAAGGGTTCCATCTATTTGTAGTTGGGTCTTTTCCA

ATCGTTTCTTCTTTTTGAGGGCTTGGAGTGCAACTCTTTTATTTTTCGA

CGCATTTTTCTTTGCaagtactgcgatcgcgttaacgctttatcacgat accttctaccacatatcactaacaacatcaacactcatcactctcgacg
```
-continued
```
acatccactcgatcactactctcacacgaccgattaactcctcatccac gcggccgcctgcaggagcGCAAAGAAAAATGCGTCGAAAAATAAAAGAG

TTGCACTCCAAGCCCTCAAAAAGAAGAAACGATTGGAAAAGACCCAACT

ACAAATAGATGGAACCCTTACAACTATTGAAATGCAGAGGGAAGCCCTC

GAAGGAGCTAGCACAAATACTGCTGTATTAGATTCTATGAAAAATGCTG

CAGATGCCCTTAAGAAAGCTCATAAGAATTTGAATGTAGATGATGTTCA

CGATATCATGGATAagcttgccatctgattcttgcaagatcagctgagc aataactagcataacccatggggcctctaaacgggtcttgaggggtttt ttgctgaaaggaggaactatatccgga
```

Nucleotides 1-17 encode the T7 promoter; nucleotides 21-260 encode an anti-sense sequence which is substantially complementary to a target nucleotide sequence of a Corn rootworm (*Diabrotica virgifera*) gene; nucleotides 261-410 encode a loop-forming region; nucleotides 411-650 encode a sense sequence which is substantially identical to a target nucleotide sequence of a Corn rootworm (*Diabrotica vir-*

*gifera*) a gene; nucleotides 659-668 encode PTH-teminator; nucleotides 681-764 encode pET-T7 terminator.

*E. coli* HT115 (DE3) cells are transformed with two plasmids, one carrying the DV49 dsRNA expression construct and the other carrying T7 RNA polymerase under the control of an inducible element (IPTG-inducible T7 polymerase). The cells are grown to a desired cell density and the dsRNA yield is determined. The DV49 dsRNA expressing cells are heated to a temperature of at least 59° C. for 30 minutes to kill the cells. The DV49 dsRNA expressing cells are titrated to provide compositions having increasing concentrations dsRNA, for example, 0.00002, 0.001, and 0.005 mg/ml, and compositions containing the heat-killed DV49 dsRNA expressing cells or heat-killed *E. coli* HT115 (DE3) control cells are provided in the diet of Corn root worm larvae. Larval mortality and morbidity are evaluated, and mass of surviving larvae is determined. Death, stunting, or other inhibition of the Corn root worm larvae following ingestion of heat-killed DV49 dsRNA expressing cells compared to control cells indicates that ingestion of heat-killed DV49 dsRNA expressing cells is effective for controlling Corn root worm infestations.

Example 8

Bioefficacy of Lysed Vs Unlysed Bacteria

A culture of pCPB-hp+2T *E. coli* HT115 (DE3) is prepared and the cells are heat-killed as described in Example 4. An aliquot of the heat-killed pCPB-hp+2T *E. coli* HT115 (DE3) cells are then to lysed by chemical, enzymatic, freeze-thawing or mechanical means to produce a cell lysate. An aliquot of the cell lysate is then partially purified by centrifugation to remove cell debris. Three samples, unlysed heat-killed pCPB-hp+2T *E. coli* HT115 (DE3) cells, unpurified cell lysate and partially purified cell lysate are then tested for bioefficacy against Colorado potato beetle (CPB), *Leptinotarsa decemlineata* as described in Example 6 above. Aliquots of the three samples are additionally subjected to different preparations, such as lyophilization or freezing, and temperatures, such as room temperature, 4° C. and 0° C., for increasing lengths of time and the bioefficacy of the samples subjected to the various preparations and storage conditions are determined by performing biossays as described in Example 6 above. The bioefficacy of the different sample preparations are compared and a preparation showing a high degree of bioefficacy and stability is selected.

Example 9

Optimizing dsRNA Yield—Number and Combination of Terminators

A plasmid vector for efficient dsRNA production is constructed by inserting at a position 3' to a dsRNA encoding sequence, 2, 3, 4, 5, or 6 transcriptional termination sequences that are each, independently, selected from a group consisting of: PTH-terminator, pET-T7 terminator, T3-Tφ terminator, pBR322-P4 terminator, vesicular stomatitus virus terminator, rrnB-T1 terminator, rrnC terminator, TTadc transcriptional terminator such that the transcriptional terminator sequences form a functional combination with the promoter.

Host cells are transformed with the engineered vectors and transcription of the dsRNA encoding sequence from the promoter is induced. The termination efficiency of each number and combination of transcriptional termination sequences is determined. A minimum number and combination of termination sequences showing the highest termination efficiency is selected as a high termination efficiency minimizes non-productive read through of vector sequence and improves the yield of dsRNA as compared to low termination efficiency.

Example 10

Optimizing dsRNA Yield—Size of Plasmid

A plasmid vector for efficient dsRNA production is constructed by inserting an engineered dsRNA expression construct, which comprises a promoter, a dsRNA encoding element, and two or more termination sequences, into a minimal plasmid vector that does not contain a protein-based selectable marker and/or nonessential spacer sequences. Where the expected size of the vector containing the engineered dsRNA expression construct falls below a minimum size for efficient plasmid replication, one or more additional engineered dsRNA expression constructs or dsRNA encoding elements are inserted into the vector to achieve a minimum size for efficient replication of the resultant expression vector. Host cells are transformed with the dsRNA expression vector. If needed, a vector encoding an RNA polymerase which drives dsRNA transcription from the dsRNA expression vector is co-transformed. The minimal vector backbone provides a reduced template for non-productive read through of non-dsRNA encoding sequence, improving the yield of dsRNA as compared to a plasmid with a larger percentage of vector backbone.

Example 11

Optimizing dsRNA Yield—Linearized Template

Figure 9:
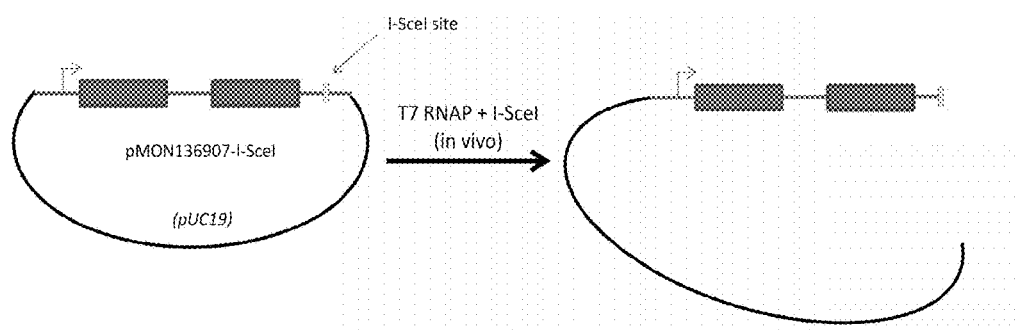
FIG. 9 depicts a schematic representation of a plasmid vector that comprises a sense DNA fragment and a complementary anti-sense DNA fragment inserted between the 3' end of a promoter and a nuclease recognition site. Expression of the nuclease linearizes the vector.

A plasmid vector for efficient dsRNA production is constructed by inserting a restriction site for an endonuclease that does not cut the host cell genome (e.g., I-SceI, which does not have any sites in the *E. coli* genome, a ZFN restriction site, or a TALEN restriction site) at a position which is 3' to a dsRNA encoding sequence that is operably linked to a promoter. See, e.g., FIG. 9. Host cells are co-transformed with the dsRNA+endonuclease production vector and a vector encoding an endonuclease which recognizes the restriction site. In some instances, expression of the endonuclease is inducible and the endonuclease may be encoded on a vector that further encodes an RNA polymerase which drives dsRNA production. Expression of the endonulease linearizes the dsRNA production vector, thereby eliminating non-productive read through of vector sequence and improving the yield of dsRNA as compared to a non-linearized plasmid.

What is claimed is:

1. An engineered dsRNA expression construct comprising:
   a. a promoter;
   b. a dsRNA encoding region positioned transcriptionally downstream of the promoter, wherein the dsRNA encoding region comprises a first, sense-oriented, nucleotide sequence, which substantially corresponds to a target sequence, a second, anti-sense-oriented nucleotide sequence, which is substantially complementary to the target sequence, and a third nucleotide sequence, which is flanked by the first and second nucleotide sequences and which encodes one or more nucleotides of a loop-region of an RNA transcript;
   c. a transcription terminator sequence, positioned 3' to the dsRNA encoding region, wherein said transcription terminator sequence comprises a PTH terminator sequence, a first pET-T7 terminator sequence, and a second pET-T7 terminator sequence, wherein at least one pET-T7 terminator sequence is positioned 3' to the PTH-terminator, wherein the transcription terminator sequence comprises nucleotides 659-764 of SEQ ID NO: 4; and
   wherein the dsRNA encoding region and the transcription terminator are operably linked to the promoter.

2. The engineered dsRNA expression construct of claim 1, wherein the engineered dsRNA expression construct further comprises one or more Zinc finger nuclease (ZFN), TAL-effector nuclease (TALEN) or meganuclease restriction sites positioned 3' to the second transcription terminator sequence.

3. The engineered dsRNA expression construct of claim 1, wherein the engineered dsRNA expression construct further comprises 1, 2, 3 or more additional transcription terminator sequence(s) positioned 3' to the dsRNA encoding region.

4. The engineered dsRNA expression construct of claim 3, wherein the additional transcription terminator sequences are each, independently, selected from a group consisting of PTH-terminator, pET-T7 terminator, T3-Tφ terminator, pBR322-P4 terminator, vesicular stomatitus virus terminator, rrnB-T1 terminator, rrnC terminator, and TTadc transcriptional terminator, such that the promoter and transcription terminator sequences form a functional combination.

5. The engineered dsRNA expression construct of claim 1, wherein the promoter is a bacteriophage promoter.

6. The engineered dsRNA expression construct of claim 1, wherein the dsRNA encoding region comprises SEQ ID NO 2.

7. A vector comprising the engineered dsRNA expression construct of claim 1, wherein the vector is a plasmid vector.

8. A bacterial host cell comprising the vector of claim 7.

9. The bacterial host cell of claim 8, wherein the bacterial host cell does not express RNAse A.

10. A cell culture system for in vivo synthesis of dsRNA comprising the bacterial host cell of claim 8 and a growth media.

11. The cell culture system of claim 10, wherein the growth media comprises 3.2% Tryptone, 2% Yeast Extract, 0.5% NaCl, 1% glycerol, 0.1% glucose, 0.4% alpha-lactose, 50 mM (NH4)2SO4, 10 mM KH2PO4, 40 mM Na2HPO4, 2 mM MgSO4.

12. A composition for controlling an invertebrate pest infestation comprising the bacterial host cell of claim 8, wherein the bacterial host cell is dead and un-lysed.

13. A composition for controlling an invertebrate pest infestation comprising a lysate of the bacterial host cell of claim 8.

14. A method for controlling an invertebrate pest infestation comprising applying the composition of claim 12 to a plant.

15. A composition for inhibiting the spread of a viral disease in a population of plants comprising a lysate of the bacterial host cell of claim 8.

16. A method for inhibiting the spread of a viral disease in a population of plants comprising applying the composition of claim 15 to a plant, wherein the plant is a food source for an insect or nematode vector of the virus.

* * * * *

SEQUENCE LISTING

<160> NUMBER OF SEQ ID NOS: 4

<210> SEQ ID NO 1
<211> LENGTH: 379
<212> TYPE: DNA
<213> ORGANISM: Leptinotarsa decemlineata

<400> SEQUENCE: 1

```
cgtaaccgcg gtttgtttcc accctgaact acctgtggct ctcacaggca gcgaagatgg      60
taccgttaga gtttggcata cgaatacaca cagattagag aattgtttga attatgggtt     120
cgagagagtg tggaccattt gttgcttgaa gggttcgaat aatgtttctc tggggtatga     180
cgagggcagt atattagtga aagttggaag agaagaaccg gcagttagta tggatgccag     240
tggcggtaaa ataatttggg caaggcactc ggaattacaa caagctaatt tgaaggcgct     300
gccagaaggt ggagaaataa gagatgggga gcgtttacct gtctctgtaa aagatatggg     360
agcatgtgaa atatcccct                                                  379
```

<210> SEQ ID NO 2
<211> LENGTH: 713
<212> TYPE: DNA
<213> ORGANISM: artificial sequence
<220> FEATURE:
<223> OTHER INFORMATION: synthetic

<400> SEQUENCE: 2

```
gggtacctgt ggctctcaca ggcagcgaag atggtaccgt tagagtttgg catacgaata      60
cacacagatt agagaattgt ttgaattatg ggttcgagag agtgtggacc atttgttgct     120
tgaagggttc gaataatgtt tctctggggt atgacgaggg cagtatatta gtgaaagttg     180
gaagagaaga accggcagtt agtatggatg ccagtggcgg taaaataatt tgggcaaggc     240
actcggaatt acaacaagct aatttgaagg cgctgccaga aggaagtact gcgatcgcgt     300
taacgcttta tcacgatacc ttctaccaca tatcactaac aacatcaaca ctcatcactc     360
tcgacgacat ccactcgatc actactctca cacgaccgat taactcctca tccacgcggc     420
cgcctgcagg agcccttctg gcagcgcctt caaattagct tgttgtaatt ccgagtgcct     480
tgcccaaatt attttaccgc cactggcatc catactaact gccggttctt ctcttccaac     540
tttcactaat atactgccct cgtcataccc cagagaaaca ttattcgaac ccttcaagca     600
acaaatggtc cacactctct cgaacccata attcaaacaa ttctctaatc tgtgtgtatt     660
cgtatgccaa actctaacgg taccatcttc gctgcctgtg agagccacag gta            713
```

<210> SEQ ID NO 3
<211> LENGTH: 844
<212> TYPE: DNA
<213> ORGANISM: artificial sequence
<220> FEATURE:
<223> OTHER INFORMATION: synthetic

<400> SEQUENCE: 3

```
taatacgact cactataggg tacctgtggc tctcacaggc agcgaagatg gtaccgttag      60
agtttggcat acgaatacac acagattaga gaattgtttg aattatgggt tcgagagagt     120
gtggaccatt tgttgcttga agggttcgaa taatgtttct ctggggtatg acgagggcag     180
tatattagtg aaagttggaa gagaagaacc ggcagttagt atggatgcca gtggcggtaa     240
aataatttgg gcaaggcact cggaattaca acaagctaat ttgaaggcgc tgccagaagg     300
aagtactgcg atcgcgttaa cgctttatca cgatacctt taccacatat cactaacaac     360
```

```
atcaacactc atcactctcg acgacatcca ctcgatcact actctcacac gaccgattaa    420
ctcctcatcc acgcggccgc ctgcaggagc ccttctggca gcgccttcaa attagcttgt    480
tgtaattccg agtgccttgc ccaaattatt ttaccgccac tggcatccat actaactgcc    540
ggttcttctc ttccaacttt cactaatata ctgccctcgt catacccag agaaacatta     600 ttcgaaccct tcaagcaaca aatggtccac actctctcga acccataatt caaacaattc    660
tctaatctgt gtgtattcgt atgccaaact ctaacggtac catcttcgct gcctgtgaga    720
gccacaggta aagcttgcca tctgtttct tgcaagatca gctgagcaat aactagcata     780
accccttggg gcctctaaac gggtcttgag gggttttttg ctgaaaggag gaactatatc    840
cgga                                                                  844

<210> SEQ ID NO 4
<211> LENGTH: 764
<212> TYPE: DNA
<213> ORGANISM: artificial sequence
<220> FEATURE:
<223> OTHER INFORMATION: synthetic

<400> SEQUENCE: 4
taatacgact cactataggg atccatgata tcgtgaacat catctacatt caaattctta     60
tgagctttct taagggcatc tgcagcattt ttcatagaat ctaatacagc agtatttgtg    120
ctagctcctt cgagggcttc cctctgcatt tcaatagttg taagggttcc atctatttgt    180
agttgggtct tttccaatcg tttcttcttt ttgagggctt ggagtgcaac tcttttattt    240
ttcgacgcat ttttctttgc aagtactgcg atcgcgttaa cgctttatca cgataccttc    300
taccacatat cactaacaac atcaacactc atcactctcg acgacatcca ctcgatcact    360
actctcacac gaccgattaa ctcctcatcc acgcggccgc ctgcaggagc gcaaagaaaa    420
atgcgtcgaa aaataaaaga gttgcactcc aagccctcaa aaagaagaaa cgattggaaa    480
agacccaact acaaatagat ggaaccctta caactattga aatgcagagg gaagccctcg    540
aaggagctag cacaaatact gctgtattag attctatgaa aaatgctgca gatgccctta    600
agaaagctca taagaatttg aatgtagatg atgttcacga tatcatggat aagcttgcca    660
tctgttttct tgcaagatca gctgagcaat aactagcata accccttggg gcctctaaac    720
gggtcttgag gggttttttg ctgaaaggag gaactatatc cgga                     764
```